US010105573B2

(12) United States Patent
Park et al.

(10) Patent No.: US 10,105,573 B2
(45) Date of Patent: Oct. 23, 2018

(54) WATCH-TYPE MOBILE TERMINAL AND METHOD FOR CONTROLLING SAME

(71) Applicant: LG ELECTRONICS INC., Seoul (KR)

(72) Inventors: Mihyun Park, Seoul (KR); Mansoo Sin, Seoul (KR); Woonghee Park, Seoul (KR); Youngsok Lee, Seoul (KR); Gukchan Lim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/738,088

(22) PCT Filed: Jun. 30, 2015

(86) PCT No.: PCT/KR2015/006697
§ 371 (c)(1),
(2) Date: Dec. 19, 2017

(87) PCT Pub. No.: WO2017/002989
PCT Pub. Date: Jan. 5, 2017

(65) Prior Publication Data
US 2018/0154212 A1 Jun. 7, 2018

(51) Int. Cl.
*G08C 19/22* (2006.01)
*H04Q 9/00* (2006.01)
(Continued)

(52) U.S. Cl.
CPC ........ *A63B 24/0062* (2013.01); *A61B 5/1118* (2013.01); *A61B 5/681* (2013.01);
(Continued)

(58) Field of Classification Search
CPC .................................................. G06F 19/3406
(Continued)

(56) References Cited

U.S. PATENT DOCUMENTS

2012/0253755 A1* 10/2012 Gobel .................... G16H 50/30
  703/2
2014/0168266 A1*  6/2014 Kimura ............. G02B 27/0172
  345/633
2015/0054716 A1*  2/2015 Hirabayashi ....... G02B 27/0093
  345/8

FOREIGN PATENT DOCUMENTS

JP         2013239115       11/2013
KR       1020090060861       6/2009
(Continued)

OTHER PUBLICATIONS

PCT International Application No. PCT/KR2015/006697, Written Opinion of the International Searching Authority dated Mar. 28, 2016, 22 pages.

*Primary Examiner* — Fabricio R Murillo Garcia
(74) *Attorney, Agent, or Firm* — Lee, Hong, Degerman, Kang & Waimey PC

(57) ABSTRACT

The present invention relates to a watch-type mobile terminal and a method for controlling the same. More specifically, the present invention relates to a watch-type mobile terminal which displays an activity amount, an exercise amount, and the physical age in the daily life of a user; and a method for controlling the same. In order to achieve the objective and other objectives, a watch-type mobile terminal according to one aspect of the present invention, comprises: a display unit; a sensing unit for sensing exercise information of a user and an input signal; and a control unit, wherein the control unit determines, from the exercise information, a first state in which a user is in the middle of daily activities, or a second state in which the user is in the middle of a predefined exercise. In case of the first state, the display unit displays a first indicator which represents a real-time activity amount. In the case of the second state, the display unit (Continued)

(a)

(b)

displays a second indicator which represents exercise efficiency.

16 Claims, 21 Drawing Sheets

(51) Int. Cl.
 *A63B 24/00*   (2006.01)
 *G06Q 50/22*   (2018.01)
 *H04M 1/725*   (2006.01)
 *A61B 5/11*   (2006.01)
 *A61B 5/00*   (2006.01)
 *G08B 5/22*   (2006.01)
 *A61B 5/024*   (2006.01)
 *G06F 3/041*   (2006.01)

(52) U.S. Cl.
 CPC ......... *A63B 24/0075* (2013.01); *G06Q 50/22* (2013.01); *G08B 5/228* (2013.01); *H04M 1/725* (2013.01); *A61B 5/02438* (2013.01); *A63B 2220/17* (2013.01); *A63B 2220/40* (2013.01); *A63B 2220/72* (2013.01); *A63B 2220/74* (2013.01); *A63B 2220/75* (2013.01); *A63B 2220/803* (2013.01); *A63B 2220/805* (2013.01); *A63B 2220/808* (2013.01); *A63B 2225/15* (2013.01); *A63B 2225/50* (2013.01); *A63B 2230/06* (2013.01); *A63B 2230/75* (2013.01); *G06F 3/041* (2013.01); *G06F 2203/04101* (2013.01); *G06F 2203/04102* (2013.01)

(58) Field of Classification Search
 USPC ..................................................... 340/870.07
 See application file for complete search history.

(56) References Cited

FOREIGN PATENT DOCUMENTS

| | | |
|---|---|---|
| KR | 1020130088670 | 8/2013 |
| KR | 1020150045768 | 4/2015 |
| KR | 1020150062761 | 6/2015 |

\* cited by examiner (a)　　　　　(b)　　　　　(c)

(a)　　　　　(b)

(a)  (b)  (c)

(a)  (b)  (c)

(a)  (b)

(a)  (b)  (c)

(a)  (b)

(a)  (b)

(a)          (b)

(a)          (b)

(a)  (b)

FIG. 24
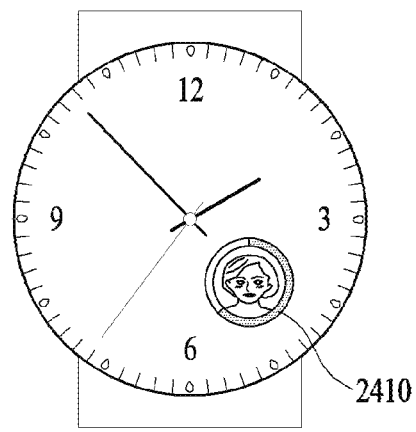
(a)
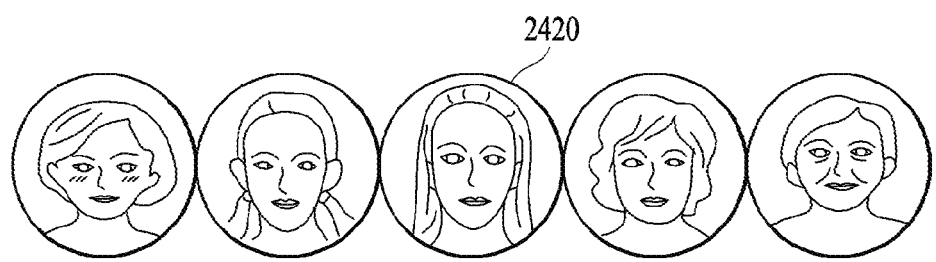
(b)

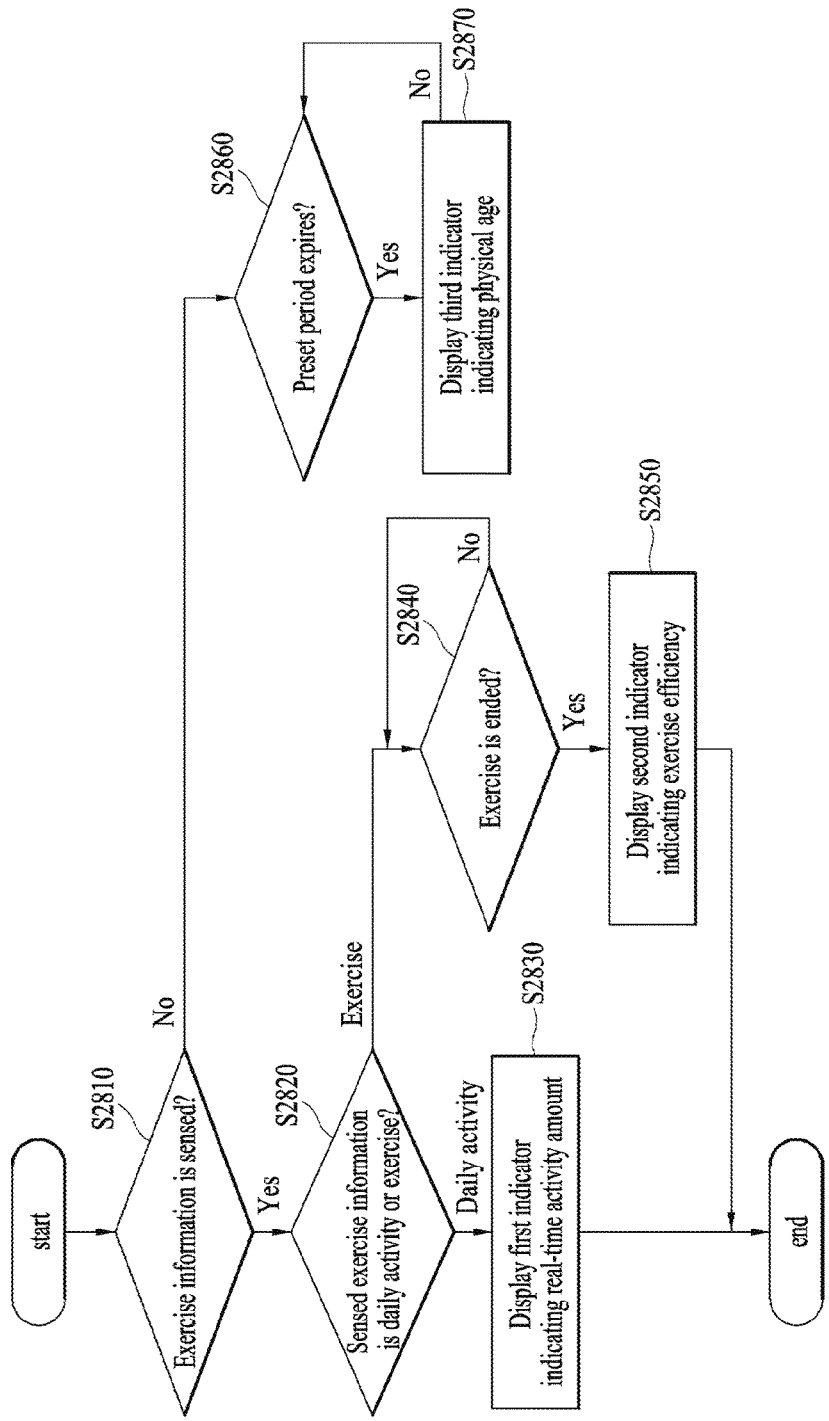

WATCH-TYPE MOBILE TERMINAL AND METHOD FOR CONTROLLING SAME

CROSS-REFERENCE TO RELATED APPLICATIONS

This application is the National Stage filing under 35 U.S.C. 371 of International Application No. PCT/KR2015/006697, filed on Jun. 30, 2015, the contents of which are hereby incorporated by reference herein its entirety.

TECHNICAL FIELD

The present invention relates to a watch-type mobile terminal and method for controlling the same, and more particularly, to a watch-type mobile terminal configured to display an activity amount, an exercise amount and a physical age in user's daily life and method for controlling the same.

BACKGROUND ART

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

As such a terminal is functionally diversified, it is implemented into a multimedia player equipped with complex functions such as photo or video shot, music or video file playback, game, broadcast reception and the like.

Efforts are ongoing to support and increase the functionality of mobile terminals. Such efforts include software and hardware improvements, as well as changes and improvements in the structural components.

Meanwhile, in case of a related art watch-type mobile terminal, various healthcare applications are provided to record exercise history only. And, the demand for motivating a user currently wearing a watch-type mobile terminal to take exercise as well as recording exercise history is rising.

DISCLOSURE OF THE INVENTION

Technical Task

One technical task of the present invention is to obviate the aforementioned problem and other problems. Another technical task of the present invention is to provide a watch-type mobile terminal and method for controlling the same, by which a first indicator indicating a real-time activity amount according to a level of user's movement and a second indicator indicating exercise efficiency are displayed in a manner of distinguishing an exercise situation and a daily activity from each other.

Another technical task of the present invention is to provide a watch-type mobile terminal and method for controlling the same, by which a third indicator indicating a user's physical age per preset period is displayed based on user's daily life vitality and exercise efficiency.

Another technical task of the present invention is to provide a watch-type mobile terminal and method for controlling the same, by which an exercise guide for complementing or maintaining physical strength on the basis of a level of user's movement in daily life is provided.

Further technical task of the present invention is to provide a watch-type mobile terminal and method for controlling the same, by which a compensation indicator is displayed according to an achievement level of a user's goal activity amount.

Technical Solutions

In one technical aspect of the present invention, provided herein is a watch-type mobile terminal, including a display unit, a sensing unit sensing user's exercise information and an input signal, and a controller configured to determine a first state that a user is taking daily activity or a second state that the user is taking preset exercise from the exercise information, display a first indicator indicating a real-time activity amount on the display unit in case of the first state, and display a second indicator indicating exercise efficiency on the display unit in case of the second state.

In another technical aspect of the present invention, provided herein is a method of controlling a watch-type mobile terminal, including sensing user's exercise information, determining a first state that a user is taking daily activity or a second state that the user is taking preset exercise from the exercise information, displaying a first indicator indicating a real-time activity amount on the display unit in case of the first state, and displaying a second indicator indicating exercise efficiency on the display unit in case of the second state.

Advantageous Effects

Effects of a watch-type mobile terminal and method for controlling the same according to the present invention are described as follows.

According to at least one of embodiments of the present invention, by determining whether user's movement is in the course of daily life or exercise, user's efficiency in each state can be intuitively represented in a manner of being displayed on a watch screen.

According to at least one of embodiments of the present invention, based on user's exercise efficiency and daily life vitality, comprehensive evaluation of user's overall life cycle can be provided.

According to at least one of embodiments of the present invention, by providing real-time evaluation of daily life movement or exercise, a user can be motivated to take exercise.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

DESCRIPTION OF DRAWINGS

FIG. 24 is a diagram for one example of a third indicator indicating a physical age in a watch-type mobile terminal related to the present invention.

FIG. 28 is a flowchart for a method of controlling a watch-type mobile terminal related to the present invention.

BEST MODE FOR INVENTION

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1A:
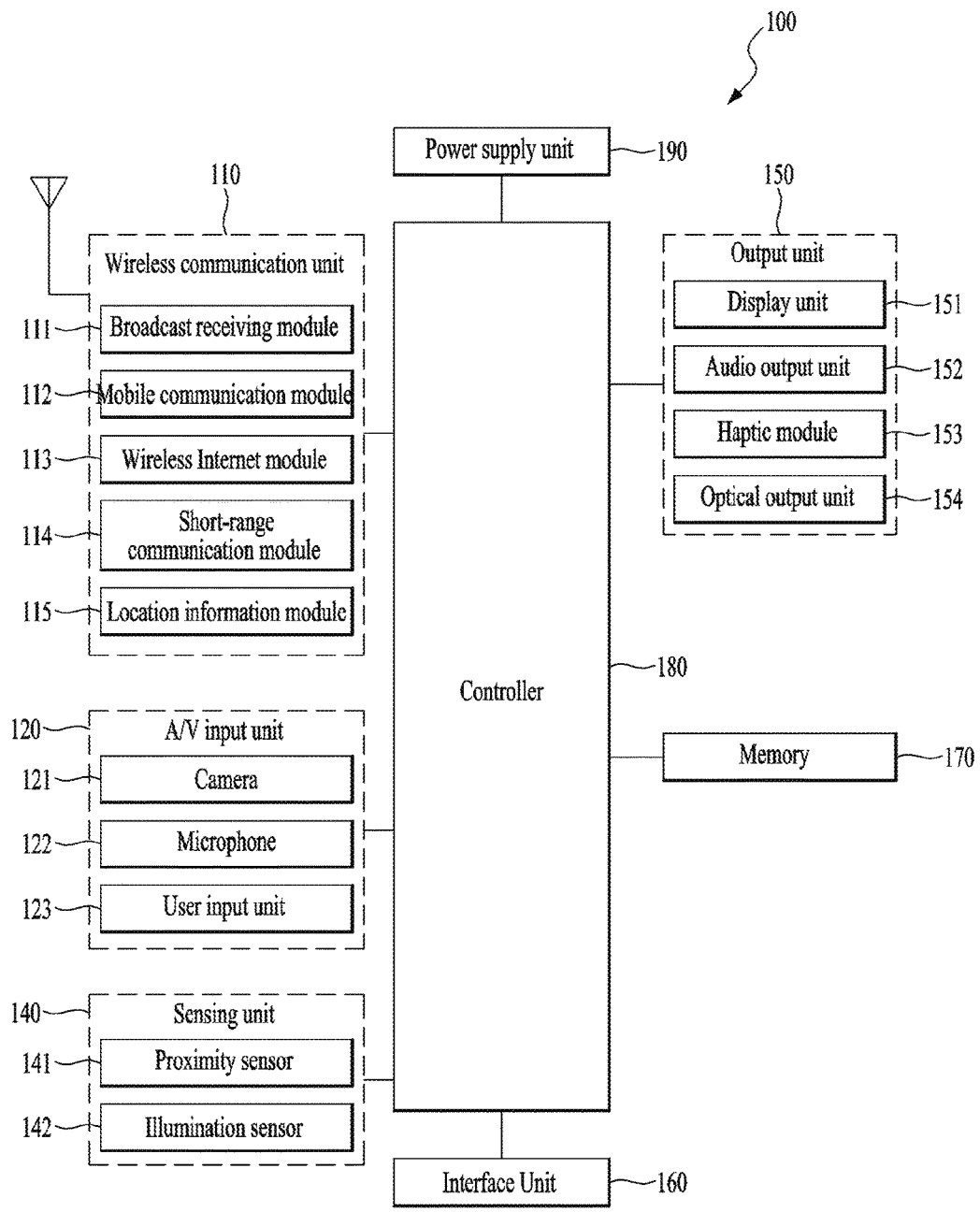
FIG. 1A is a block diagram of a mobile terminal in accordance with the present disclosure.
Figure 1B:
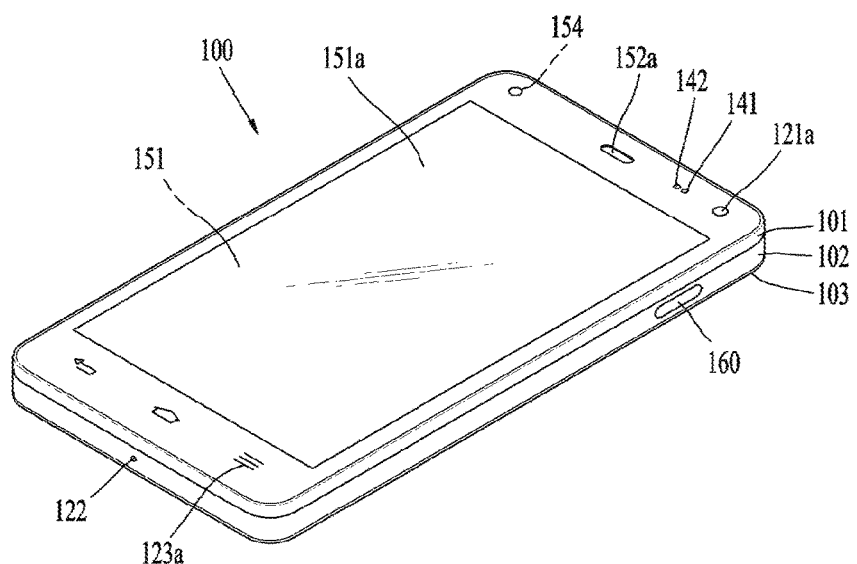
FIGS. 1B and 1C are conceptual views of one example of the mobile terminal, viewed from different directions.
Figure 1C:
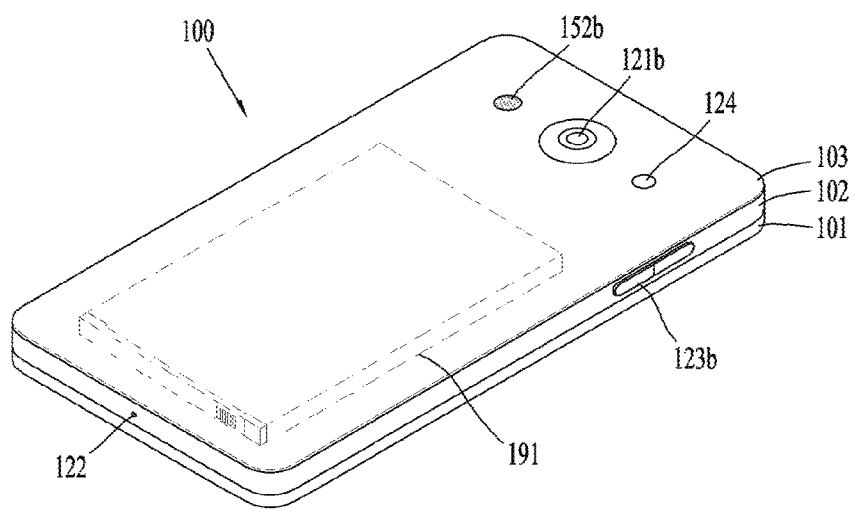

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented. Referring now to FIG. 1A, the mobile terminal 100 is shown having wireless communication unit 110 configured with several commonly implemented components.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142. If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 processes signals, data, and informations inputted or outputted through the components mentioned in the foregoing description or runs an application program saved in the memory 170, thereby providing or processing an information or function appropriate for to a user.

The controller 180 may provide or process information or functions appropriate for a user by processing signals, data, information and the like, which are input or output by the various components depicted in FIG. 1A, or activating application programs stored in the memory 170. As one example, the controller 180 controls some or all of the components illustrated in FIG. 1A according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least one portion of the respective components can cooperatively operate to implement operations, controls or controlling methods of a mobile terminal according to various embodiments of the present invention mentioned in the following description. The operations, controls or controlling methods of the mobile terminal can be implemented on the mobile terminal by running at least one application program saved in the memory 170.

Referring still to FIG. 1A, various components depicted in this figure will now be described in more detail.

Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The broadcast managing entity may be implemented using a server or system which generates and transmits a broadcast signal and/or broadcast associated information, or a server which receives a pre-generated broadcast signal and/or broadcast associated information, and sends such items to the mobile terminal. The broadcast signal may be implemented using any of a TV broadcast signal, a radio broadcast signal, a data broadcast signal, and combinations thereof, among others. The broadcast signal in some cases may further include a data broadcast signal combined with a TV or radio broadcast signal.

The broadcast signal may be encoded according to any of a variety of technical standards or broadcasting methods (for example, International Organization for Standardization (ISO), International Electrotechnical Commission (IEC), Digital Video Broadcast (DVB), Advanced Television Systems Committee (ATSC), and the like) for transmission and reception of digital broadcast signals. The broadcast receiving module 111 can receive the digital broadcast signals using a method appropriate for the transmission method utilized.

Examples of broadcast associated information may include information associated with a broadcast channel, a broadcast program, a broadcast event, a broadcast service provider, or the like. The broadcast associated information may also be provided via a mobile communication network, and in this case, received by the mobile communication module 112.

The broadcast associated information may be implemented in various formats. For instance, broadcast associated information may include an Electronic Program Guide (EPG) of Digital Multimedia Broadcasting (DMB), an Electronic Service Guide (ESG) of Digital Video Broadcast-Handheld (DVB-H), and the like. Broadcast signals and/or broadcast associated information received via the broadcast receiving module 111 may be stored in a suitable device, such as a memory 170.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal. As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others. As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

In general, a 3D stereoscopic image may include a left image (e.g., a left eye image) and a right image (e.g., a right eye image). According to how left and right images are combined into a 3D stereoscopic image, a 3D stereoscopic imaging method can be divided into a top-down method in which left and right images are located up and down in a frame, an L-to-R (left-to-right or side by side) method in which left and right images are located left and right in a frame, a checker board method in which fragments of left and right images are located in a tile form, an interlaced method in which left and right images are alternately located by columns or rows, and a time sequential (or frame by frame) method in which left and right images are alternately displayed on a time basis.

Also, as for a 3D thumbnail image, a left image thumbnail and a right image thumbnail can be generated from a left image and a right image of an original image frame, respectively, and then combined to generate a single 3D thumbnail image. In general, the term "thumbnail" may be used to refer to a reduced image or a reduced still image. A generated left image thumbnail and right image thumbnail may be displayed with a horizontal distance difference there between by a depth corresponding to the disparity between the left image and the right image on the screen, thereby providing a stereoscopic space sense.

A left image and a right image required for implementing a 3D stereoscopic image may be displayed on the stereoscopic display unit using a stereoscopic processing unit. The stereoscopic processing unit can receive the 3D image and extract the left image and the right image, or can receive the 2D image and change it into a left image and a right image.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors.

The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal.

In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

The mobile terminal 100 may be equipped with the display unit 151, the $1^{st}$ audio output unit 152a, the $2^{nd}$ audio output unit 152b, the proximity sensor 141, the illumination sensor 142, the optical output unit 154, the $1^{st}$ camera 121a, the $2^{nd}$ camera 121b, the $1^{st}$ manipulating unit 123a, the $2^{nd}$ manipulating unit 123b, the microphone 122, the interface unit 160, and the like.

FIGS. 1B and 1C depict certain components as arranged on the mobile terminal.

However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. The display unit 151 may be implemented using one or more suitable display devices.

Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a.

The first audio output module 152a may be implemented in the form of a speaker to output voice audio, alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this case, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit (not shown) may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

As shown in FIG. 1C, a flash 124 is shown adjacent to the second camera 121b. When an image of a subject is captured with the camera 121b, the flash 124 may illuminate the subject.

As shown in FIG. 1B, the second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160.

Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

Meanwhile, in the present invention, information processed by a mobile terminal can be displayed using a flexible display. This is described in detail with reference to the accompanying drawings as follows.

Figure 2:
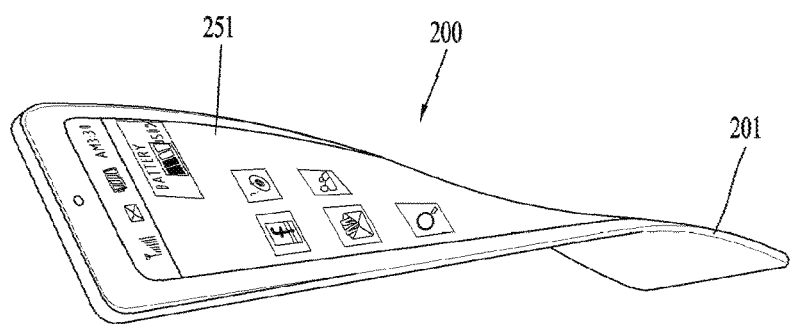
FIG. 2 is a conceptual view of a deformable mobile terminal according to an alternative embodiment of the present disclosure.

FIG. 2 is a conceptual view of a deformable mobile terminal according to an alternative embodiment of the present invention.

In this figure, mobile terminal 200 is shown having display unit 251, which is a type of display that is deformable by an external force. This deformation, which includes display unit 251 and other components of mobile terminal 200, may include any of curving, bending, folding, twisting, rolling, and combinations thereof. The deformable display unit 251 may also be referred to as a "flexible display unit." In some implementations, the flexible display unit 251 may include a general flexible display, electronic paper (also known as e-paper), and combinations thereof. In general, mobile terminal 200 may be configured to include features that are the same or similar to that of mobile terminal 100 of FIGS. 1A-1C.

The flexible display of mobile terminal 200 is generally formed as a lightweight, non-fragile display, which still exhibits characteristics of a conventional flat panel display, but is instead fabricated on a flexible substrate which can be deformed as noted previously.

The term e-paper may be used to refer to a display technology employing the characteristic of a general ink, and is different from the conventional flat panel display in view of using reflected light. E-paper is generally understood as changing displayed information using a twist ball or via electrophoresis using a capsule.

When in a state that the flexible display unit 251 is not deformed (for example, in a state with an infinite radius of curvature and referred to as a first state), a display region of the flexible display unit 251 includes a generally flat surface. When in a state that the flexible display unit 251 is deformed from the first state by an external force (for example, a state with a finite radius of curvature and referred to as a second state), the display region may become a curved surface or a bent surface. As illustrated, information displayed in the second state may be visual information output on the curved surface. The visual information may be realized in such a manner that a light emission of each unit pixel (sub-pixel) arranged in a matrix configuration is controlled independently. The unit pixel denotes an elementary unit for representing one color.

According to one alternative embodiment, the first state of the flexible display unit 251 may be a curved state (for example, a state of being curved from up to down or from right to left), instead of being in flat state. In this embodiment, when an external force is applied to the flexible display unit 251, the flexible display unit 251 may transition to the second state such that the flexible display unit is deformed into the flat state (or a less curved state) or into a more curved state.

If desired, the flexible display unit 251 may implement a flexible touch screen using a touch sensor in combination with the display. When a touch is received at the flexible touch screen, the controller 180 can execute certain control corresponding to the touch input. In general, the flexible touch screen is configured to sense touch and other input while in both the first and second states.

One option is to configure the mobile terminal 200 to include a deformation sensor which senses the deforming of the flexible display unit 251. The deformation sensor may be included in the sensing unit 140.

The deformation sensor may be located in the flexible display unit 251 or the case 201 to sense information related to the deforming of the flexible display unit 251. Examples of such information related to the deforming of the flexible display unit 251 may be a deformed direction, a deformed degree, a deformed position, a deformed amount of time, an acceleration that the deformed flexible display unit 251 is restored, and the like. Other possibilities include most any type of information which can be sensed in response to the curving of the flexible display unit or sensed while the flexible display unit 251 is transitioning into, or existing in, the first and second states.

In some embodiments, controller 180 or other component can change information displayed on the flexible display unit 251, or generate a control signal for controlling a function of the mobile terminal 200, based on the information related to the deforming of the flexible display unit 251. Such information is typically sensed by the deformation sensor.

The mobile terminal 200 is shown having a case 201 for accommodating the flexible display unit 251. The case 201 can be deformable together with the flexible display unit 251, taking into account the characteristics of the flexible display unit 251.

A battery (not shown in this figure) located in the mobile terminal 200 may also be deformable in cooperation with the flexible display unit 261, taking into account the characteristic of the flexible display unit 251. One technique to implement such a battery is to use a stack and folding method of stacking battery cells.

The deformation of the flexible display unit 251 not limited to perform by an external force. For example, the flexible display unit 251 can be deformed into the second state from the first state by a user command, application command, or the like.

In accordance with still further embodiments, a mobile terminal may be configured as a device which is wearable on a human body. Such devices go beyond the usual technique of a user grasping the mobile terminal using their hand. Examples of the wearable device include a smart watch, a smart glass, a head mounted display (HMD), and the like.

A typical wearable device can exchange data with (or cooperate with) another mobile terminal 100. In such a device, the wearable device generally has functionality that is less than the cooperating mobile terminal. For instance, the short-range communication module 114 of a mobile terminal 100 may sense or recognize a wearable device that is near-enough to communicate with the mobile terminal. In addition, when the sensed wearable device is a device which is authenticated to communicate with the mobile terminal 100, the controller 180 may transmit data processed in the mobile terminal 100 to the wearable device via the short-range communication module 114, for example. Hence, a user of the wearable device can use the data processed in the mobile terminal 100 on the wearable device. For example, when a call is received in the mobile terminal 100, the user can answer the call using the wearable device. Also, when a message is received in the mobile terminal 100, the user can check the received message using the wearable device.

Figure 3:
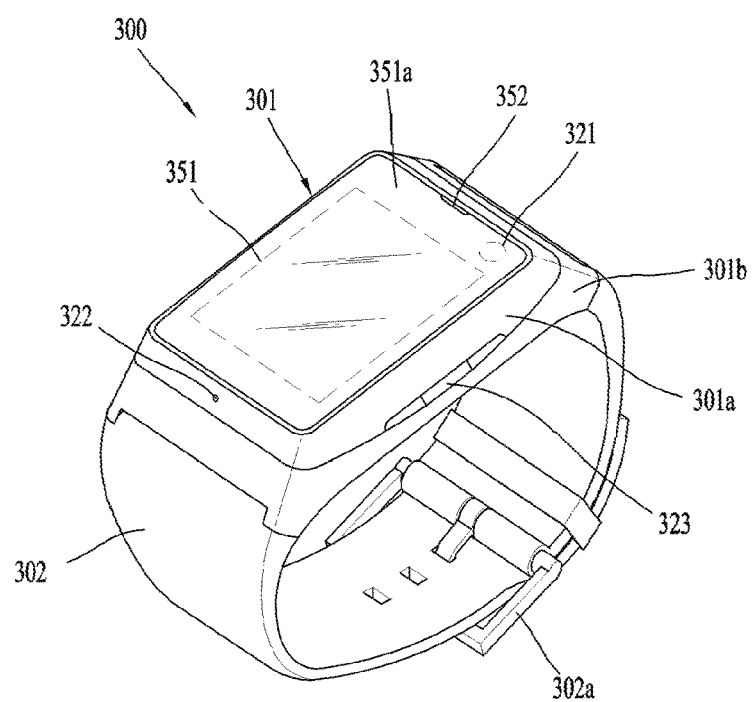
FIG. 3 is a conceptual view of a wearable mobile terminal according to another alternative embodiment of the present disclosure.

FIG. 3 is a perspective view illustrating one example of a watch-type mobile terminal 300 in accordance with another exemplary embodiment.

As illustrated in FIG. 3, the watch-type mobile terminal 300 includes a main body 301 with a display unit 351 and a band 302 connected to the main body 301 to be wearable on a wrist. In general, mobile terminal 300 may be configured to include features that are the same or similar to that of mobile terminal 100 of FIGS. 1A-1C.

The main body 301 may include a case having a certain appearance. As illustrated, the case may include a first case 301a and a second case 301b cooperatively defining an inner space for accommodating various electronic components. Other configurations are possible. For instance, a single case may alternatively be implemented, with such a case being configured to define the inner space, thereby implementing a mobile terminal 300 with a uni-body.

The watch-type mobile terminal 300 can perform wireless communication, and an antenna for the wireless communication can be installed in the main body 301. The antenna may extend its function using the case. For example, a case including a conductive material may be electrically connected to the antenna to extend a ground area or a radiation area.

The display unit 351 is shown located at the front side of the main body 301 so that displayed information is viewable to a user. In some embodiments, the display unit 351 includes a touch sensor so that the display unit can function as a touch screen. As illustrated, window 351a is positioned on the first case 301a to form a front surface of the terminal body together with the first case 301a.

The illustrated embodiment includes audio output module 352, a camera 321, a microphone 322, and a user input unit 323 positioned on the main body 301. When the display unit 351 is implemented as a touch screen, additional function keys may be minimized or eliminated. For example, when the touch screen is implemented, the user input unit 323 may be omitted.

The band 302 is commonly worn on the user's wrist and may be made of a flexible material for facilitating wearing of the device. As one example, the band 302 may be made of fur, rubber, silicon, synthetic resin, or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion (not shown) electrically connected to the antenna to extend a ground area.

The band 302 may include fastener 302a. The fastener 302a may be implemented into a buckle type, a snap-fit hook structure, a Velcro® type, or the like, and include a flexible section or material. The drawing illustrates an example that the fastener 302a is implemented using a buckle.

Figure 4:
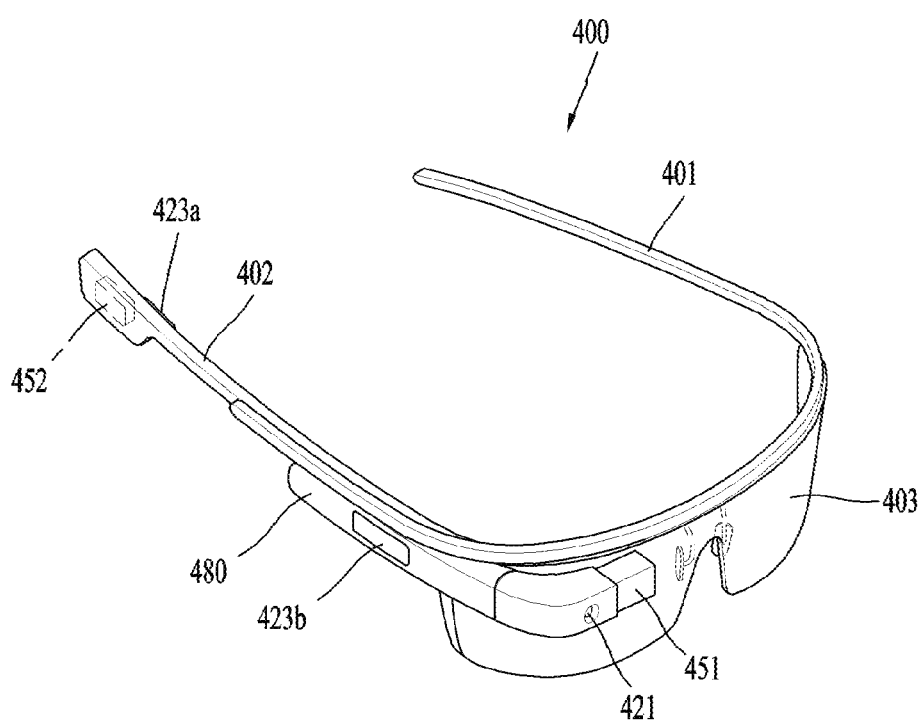
FIG. 4 is a conceptual view of a wearable mobile terminal according to another alternative embodiment of the present disclosure.

FIG. 4 is a perspective view illustrating one example of a glass-type mobile terminal 400 according to another exemplary embodiment.

The glass-type mobile terminal 400 can be wearable on a head of a human body and provided with a frame (case, housing, etc.) therefor. The frame may be made of a flexible material to be easily worn. The frame of mobile terminal 400 is shown having a first frame 401 and a second frame 402, which can be made of the same or different materials. In general, mobile terminal 400 may be configured to include features that are the same or similar to that of mobile terminal 100 of FIGS. 1A-1C.

The frame may be supported on the head and defines a space for mounting various components. As illustrated, electronic components, such as a control module 480, an audio output module 452, and the like, may be mounted to the frame part. Also, a lens 403 for covering either or both of the left and right eyes may be detachably coupled to the frame part.

The control module 480 controls various electronic components disposed in the mobile terminal 400. The control module 480 may be understood as a component corresponding to the aforementioned controller 180. FIG. 4 illustrates that the control module 480 is installed in the frame part on one side of the head, but other locations are possible.

The display unit 451 may be implemented as a head mounted display (HMD). The HMD refers to display techniques by which a display is mounted to a head to show an image directly in front of a user's eyes. In order to provide an image directly in front of the user's eyes when the user wears the glass-type mobile terminal 400, the display unit 451 may be located to correspond to either or both of the left and right eyes. FIG. 4 illustrates that the display unit 451 is located on a portion corresponding to the right eye to output an image viewable by the user's right eye.

The display unit 451 may project an image into the user's eye using a prism. Also, the prism may be formed from optically transparent material such that the user can view both the projected image and a general visual field (a range that the user views through the eyes) in front of the user.

In such a manner, the image output through the display unit 451 may be viewed while overlapping with the general visual field. The mobile terminal 400 may provide an augmented reality (AR) by overlaying a virtual image on a realistic image or background using the display.

The camera 421 may be located adjacent to either or both of the left and right eyes to capture an image. Since the camera 421 is located adjacent to the eye, the camera 421 can acquire a scene that the user is currently viewing.

The camera 421 may be positioned at most any location of the mobile terminal. In some embodiments, multiple cameras 421 may be utilized. Such multiple cameras 421 may be used to acquire a stereoscopic image.

The glass-type mobile terminal 400 may include user input units 423a and 423b, which can each be manipulated by the user to provide an input. The user input units 423a and 423b may employ techniques which permit input via a tactile input. Typical tactile inputs include a touch, push, or the like. The user input units 423a and 423b are shown operable in a pushing manner and a touching manner as they are located on the frame part and the control module 480, respectively.

If desired, mobile terminal 400 may include a microphone which processes input sound into electric audio data, and an audio output module 452 for outputting audio. The audio output module 452 may be configured to produce audio in a general audio output manner or an osteoconductive manner. When the audio output module 452 is implemented in the osteoconductive manner, the audio output module 452 may be closely adhered to the head when the user wears the mobile terminal 400 and vibrate the user's skull to transfer sounds.

A communication system which is operable with the variously described mobile terminals will now be described in more detail.

Such a communication system may be configured to utilize any of a variety of different air interfaces and/or physical layers. Examples of such air interfaces utilized by the communication system include Frequency Division Multiple Access (FDMA), Time Division Multiple Access (TDMA), Code Division Multiple Access (CDMA), Universal Mobile Telecommunications System (UMTS) (including, Long Term Evolution (LTE), LTE-A (Long Term Evolution-Advanced)), Global System for Mobile Communications (GSM), and the like.

By way of a non-limiting example only, further description will relate to a CDMA communication system, but such teachings apply equally to other system types including a CDMA wireless communication system as well as OFDM (Orthogonal Frequency Division Multiplexing) wireless communication system.

A CDMA wireless communication system generally includes one or more mobile terminals (MT or User Equipment, UE) 100, one or more base stations (BSs, NodeB, or evolved NodeB), one or more base station controllers (BSCs), and a mobile switching center (MSC). The MSC is configured to interface with a conventional Public Switched Telephone Network (PSTN) and the BSCs. The BSCs are coupled to the base stations via backhaul lines. The backhaul lines may be configured in accordance with any of several known interfaces including, for example, E1/T1, ATM, IP, PPP, Frame Relay, HDSL, ADSL, or xDSL. Hence, the plurality of BSCs can be included in the CDMA wireless communication system.

Each base station may include one or more sectors, each sector having an omni-directional antenna or an antenna pointed in a particular direction radially away from the base station. Alternatively, each sector may include two or more different antennas. Each base station may be configured to support a plurality of frequency assignments, with each frequency assignment having a particular spectrum (e.g., 1.25 MHz, 5 MHz, etc.).

The intersection of sector and frequency assignment may be referred to as a CDMA channel. The base stations may also be referred to as Base Station Transceiver Subsystems (BTSs). In some cases, the term "base station" may be used to refer collectively to a BSC, and one or more base stations. The base stations may also be denoted as "cell sites." Alternatively, individual sectors of a given base station may be referred to as cell sites.

A broadcasting transmitter (BT) transmits a broadcast signal to the mobile terminals 100 operating within the system. The broadcast receiving module 111 of FIG. 1A is typically configured inside the mobile terminal 100 to receive broadcast signals transmitted by the BT.

Global Positioning System (GPS) satellites for locating the position of the mobile terminal 100, for example, may cooperate with the CDMA wireless communication system. Useful position information may be obtained with greater or fewer satellites than two satellites. It is to be appreciated that other types of position detection technology, (i.e., location technology that may be used in addition to or instead of GPS location technology) may alternatively be implemented. If desired, at least one of the GPS satellites may alternatively or additionally be configured to provide satellite DMB transmissions.

The location information module 115 is generally configured to detect, calculate, or otherwise identify a position of the mobile terminal. As an example, the location information module 115 may include a Global Position System (GPS) module, a Wi-Fi module, or both. If desired, the location information module 115 may alternatively or additionally function with any of the other modules of the wireless communication unit 110 to obtain data related to the position of the mobile terminal.

A typical GPS module 115 can measure an accurate time and distance from three or more satellites, and accurately calculate a current location of the mobile terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites. Furthermore, the GPS module can acquire speed information in real time to calculate a current position. Sometimes, accuracy of a measured position may be compromised when the mobile terminal is located in a blind spot of satellite signals, such as being located in an indoor space. In order to minimize the effect of such blind spots, an alternative or supplemental location technique, such as Wi-Fi Positioning System (WPS), may be utilized.

The Wi-Fi positioning system (WPS) refers to a location determination technology based on a wireless local area network (WLAN) using Wi-Fi as a technology for tracking the location of the mobile terminal 100. This technology typically includes the use of a Wi-Fi module in the mobile terminal 100 and a wireless access point for communicating with the Wi-Fi module.

The Wi-Fi positioning system may include a Wi-Fi location determination server, a mobile terminal, a wireless access point (AP) connected to the mobile terminal, and a database stored with wireless AP information.

The mobile terminal connected to the wireless AP may transmit a location information request message to the Wi-Fi location determination server.

The Wi-Fi location determination server extracts the information of the wireless AP connected to the mobile terminal 100, based on the location information request message (or signal) of the mobile terminal 100. The information of the wireless AP may be transmitted to the Wi-Fi location determination server through the mobile terminal 100, or may be transmitted to the Wi-Fi location determination server from the wireless AP.

The information of the wireless AP extracted based on the location information request message of the mobile terminal 100 may include one or more of media access control (MAC) address, service set identification (SSID), received signal strength indicator (RSSI), reference signal received Power (RSRP), reference signal received quality (RSRQ), channel information, privacy, network type, signal strength, noise strength, and the like.

The Wi-Fi location determination server may receive the information of the wireless AP connected to the mobile terminal 100 as described above, and may extract wireless AP information corresponding to the wireless AP connected to the mobile terminal from the pre-established database. The information of any wireless APs stored in the database may be information such as MAC address, SSID, RSSI, channel information, privacy, network type, latitude and longitude coordinate, building at which the wireless AP is located, floor number, detailed indoor location information (GPS coordinate available), AP owner's address, phone number, and the like. In order to remove wireless APs provided using a mobile AP or an illegal MAC address during a location determining process, the Wi-Fi location determination server may extract only a predetermined number of wireless AP information in order of high RSSI.

Then, the Wi-Fi location determination server may extract (analyze) location information of the mobile terminal 100 using at least one wireless AP information extracted from the database.

A method for extracting (analyzing) location information of the mobile terminal 100 may include a Cell-ID method, a fingerprint method, a trigonometry method, a landmark method, and the like.

The Cell-ID method is used to determine a position of a wireless AP having the largest signal strength, among peripheral wireless AP information collected by a mobile terminal, as a position of the mobile terminal. The Cell-ID method is an implementation that is minimally complex, does not require additional costs, and location information can be rapidly acquired. However, in the Cell-ID method, the precision of positioning may fall below a desired threshold when the installation density of wireless APs is low.

The fingerprint method is used to collect signal strength information by selecting a reference position from a service area, and to track a position of a mobile terminal using the signal strength information transmitted from the mobile terminal based on the collected information. In order to use the fingerprint method, it is common for the characteristics of radio signals to be pre-stored in the form of a database.

The trigonometry method is used to calculate a position of a mobile terminal based on a distance between coordinates of at least three wireless APs and the mobile terminal. In order to measure the distance between the mobile terminal and the wireless APs, signal strength may be converted into distance information, Time of Arrival (ToA), Time Difference of Arrival (TDoA), Angle of Arrival (AoA), or the like may be taken for transmitted wireless signals.

The landmark method is used to measure a position of a mobile terminal using a known landmark transmitter.

In addition to these position location methods, various algorithms may be used to extract (analyze) location information of a mobile terminal.

Such extracted location information may be transmitted to the mobile terminal 100 through the Wi-Fi location determination server, thereby acquiring location information of the mobile terminal 100.

The mobile terminal 100 can acquire location information by being connected to at least one wireless AP. The number of wireless APs required to acquire location information of the mobile terminal 100 may be variously changed according to a wireless communication environment within which the mobile terminal 100 is positioned.

As previously described with regard to FIG. 1A, the mobile terminal may be configured to include short-range communication techniques such as Bluetooth™, Radio Frequency Identification (RFID), Infrared Data Association (IrDA), Ultra Wideband (UWB), ZigBee, Near Field Communication (NFC), Wireless USB (Wireless Universal Serial Bus), and the like.

A typical NFC module provided at the mobile terminal supports short-range wireless communication, which is a non-contactable type of communication between mobile terminals and generally occurs within about 10 cm. The NFC module may operate in one of a card mode, a reader mode, or a P2P mode. The mobile terminal 100 may further include a security module for storing card information, in order to operate the NFC module in a card mode. The security module may be a physical medium such as Universal Integrated Circuit Card (UICC) (e.g., a Subscriber Identification Module (SIM) or Universal SIM (USIM)), a secure micro SD and a sticker, or a logical medium (e.g., embedded Secure Element (SE)) embedded in the mobile terminal. Single Wire Protocol (SWP)-based data exchange may be performed between the NFC module and the security module.

In a case where the NFC module operates in a card mode, the mobile terminal may transmit card information on a general IC card to the outside. More specifically, if a mobile terminal having card information on a payment card (e. g, a credit card or a bus card) approaches a card reader, a short-range mobile payment may be executed. As another example, if a mobile terminal which stores card information on an entrance card approaches an entrance card reader, an entrance approval procedure may start. A card such as a credit card, a traffic card, or an entrance card may be included in the security module in the form of applet, and the security module may store card information on the card mounted therein. Card information for a payment card may include any of a card number, a remaining amount and usage history, and the like. Card information of an entrance card may include any of a user's name, a user's number (e.g., undergraduate number or staff number), an entrance history, and the like.

When the NFC module operates in a reader mode, the mobile terminal can read data from an external tag. The data received from the external tag by the mobile terminal may be coded into the NFC Data Exchange Format defined by the NFC Forum. The NFC Forum generally defines four record types. More specifically, the NFC Forum defines four Record Type Definitions (RTDs) such as smart poster, text, Uniform Resource Identifier (URI), and general control. If the data received from the external tag is a smart poster type, the controller may execute a browser (e.g., Internet browser). If the data received from the external tag is a text type, the controller may execute a text viewer. If the data received from the external tag is a URI type, the controller may execute a browser or originate a call. If the data received from the external tag is a general control type, the controller may execute a proper operation according to control content.

In some cases in which the NFC module operates in a P2P (Peer-to-Peer) mode, the mobile terminal can execute P2P communication with another mobile terminal. In this case, Logical Link Control Protocol (LLCP) may be applied to the P2P communication. For P2P communication, connection may be generated between the mobile terminal and another mobile terminal. This connection may be categorized as a connectionless mode which ends after one packet is switched, and a connection-oriented mode in which packets are switched consecutively. For a typical P2P communication, data such as an electronic type name card, address information, a digital photo and a URL, a setup parameter for Bluetooth connection, Wi-Fi connection, etc. may be switched. The P2P mode can be effectively utilized in switching data of a small capacity, because an available distance for NFC communication is relatively short.

Further preferred embodiments will be described in more detail with reference to additional drawing figures. It is understood by those skilled in the art that the present features can be embodied in several forms without departing from the characteristics thereof.

According to embodiments of FIGS. 5 to 28, by displaying user's movement level, exercise efficiency, and physical age intuitively on a watch screen of a watch-type mobile terminal, a user can be motivated to take exercise. Such a method is described in the following.

Moreover, for the embodiments of FIGS. 5 to 28, operations performed in a watch-type mobile terminal (hereinafter called 'mobile terminal') can be controlled by the controller 180 of FIG. 1A. For clarity of the following description, such operations are generally illustrated and described as performed by a mobile terminal.

First of all, an activity amount and an exercise amount described in the present invention are defined.

An activity amount (or, amount of activity) indicates user's movement sensed by a mobile terminal, and more particularly, an amount of daily movement instead of exercise intentionally taken by a user. For example, activity may include daily movement such as walking, stretching, stroll, stair climbing, hand wash, driving, makeup, cleaning, dish wash and the like. Moreover, a daily movement, which is not an exercise, can bring an exercise effect. For example, when a woman weighing about 50 kg in her twenties or thirties does shopping for 10 minutes, 22 kcal may be consumed. For example, when a woman weighing about 50 kg in her twenties or thirties does dish washing for 10 minutes, 23 kcal may be consumed.

An exercise amount (or, amount of exercise) indicates user's movement sensed in a mobile terminal, and more particularly, an amount of exercise intentionally taken by a user. For example, exercise may include user-intended exercise such as running, swimming, aerobic, soccer, climbing, pushup, stepper, etc.

Regarding this, the aforementioned daily activity and exercise may be determined by a mobile terminal on the basis of a level of user's movement. For example, exercise intentionally taken by a user indicates a case that at least one sensed exercise information corresponds to a preset range. Namely, user's daily activity may indicate a case that at least one sensed exercise information does not correspond to a preset range. On the other hand, daily activity and exercise may be set for a mobile terminal by a user.

Here, the exercise information may include at least one of a movement of a watch-type mobile terminal, a heart rate of a user wearing the watch-type mobile terminal, a moving speed of the watch-type mobile terminal, a moving distance of the watch-type mobile terminal, an altitude of the watch-type mobile terminal, an inclination of the watch-type mobile terminal, and an acceleration of the watch-type mobile terminal. For example, if a user's sensed heart rate exceeds 130 bpm, the watch-type mobile terminal may determine that exercise has been taken. In this case, if the user's heart rate is smaller than 130 bpm, the mobile terminal may determine that a user has performs daily activity instead of exercise. For example, if a sensed moving speed exceeds 5 km/h, the watch-type mobile terminal may determine that exercise has been taken. In this case, if the sensed moving speed is smaller than 5 km/h, the mobile terminal may determine that daily activity has been taken instead of exercise.

Figure 5:
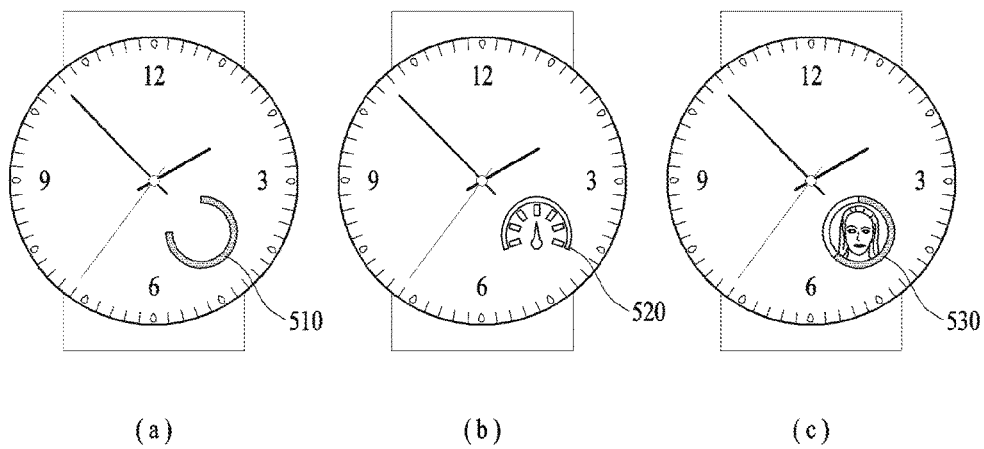
FIG. 5 is a diagram for one example of an indicator displayed in a watch-type mobile terminal related to the present invention.

FIG. 5 is a diagram for one example of an indicator displayed in a watch-type mobile terminal related to the present invention.

In the embodiments of FIGS. 5 to 28, assume that a mobile terminal is set in advance to enable an exercise related indicator to be displayed together while a watch screen is displayed. Moreover, the watch screen may correspond to a screen of a numeral-displayed digital watch as well as to a watch having hour, minute and second hands shown in FIG. 5. Meanwhile, even if a screen related to a different application is currently displayed instead of displaying a watch screen, if a condition for displaying an exercise related indicator is satisfied, the mobile terminal may display the exercise related indicator on the screen related to the different application.

In the present invention, an exercise related indicator may include a first indicator 510 indicating a user's real-time activity amount, a second indicator 520 indicating a user's exercise efficiency, and a third indicator 530 indicating a user's physical age.

First of all, referring to FIG. 5(a), a mobile terminal can display a first indicator 510 indicating user's movement in daily life. In particular, while a watch screen is displayed, the mobile terminal can display the first indicator 510 on a partial region of the watch screen. Here, the partial region, as shown in FIG. 5(a), may include a region on which the hour hand, the minute hand, the second hand and numerals are not displayed within the watch screen. Moreover, the partial region may correspond to a region outside the watch screen [not shown in FIG. 5(a)].

User's movement in daily life may correspond to a case that the aforementioned exercise information fails to correspond to a preset range. In this case, the mobile terminal determines a first state before taking exercise and is able to display the first indicator 510 on a display unit. The mobile terminal may display real activity amount over activity goal amount on the first indicator 510. The first indicator 510 shall be described in detail with reference to FIGS. 6 to 16.

Referring to FIG. 5(b), the mobile terminal may display a second indicator 520 indicating exercise efficiency after completion of exercise. In particular, while a watch screen is displayed, the mobile terminal can display the second indicator 520 on a partial region of the watch screen. The second indicator 520 may correspond to an indicator displayed after a user has taken exercise with intention of exercise. Moreover, the mobile terminal may display efficiency of exercise previously taken by a user. The second indicator 520 shall be described in detail with reference to FIGS. 17 to 22.

Referring to FIG. 5(c), after expiration of a preset period, the third indicator 530 indicating a user's physical age can be displayed. In particular, while a watch screen is displayed, the mobile terminal can display the third indicator 530 on a partial region of the watch screen. The third indicator 530 may correspond to an indicator that displays a user's physical age per preset period by synthesizing activity and exercise in daily life. The third indicator 530 shall be described in detail with reference to FIGS. 23 to 26.

Figure 6:
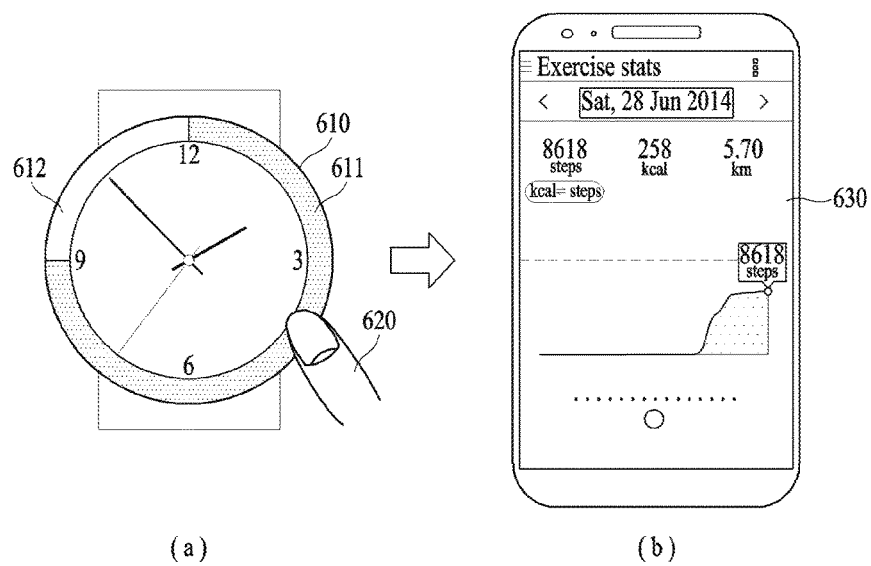
FIG. 6 is a diagram for one example of providing exercise information according to an input signal in a watch-type mobile terminal related to the present invention.

FIG. 6 is a diagram for one example of providing exercise information according to an input signal in a watch-type mobile terminal related to the present invention.

First of all, a mobile terminal may display a first indicator 610 on a display unit. Differently from the former first indicator 510 shown in FIG. 5, the first indicator 610 may be displayed outside a part of a display unit on which a watch screen is displayed. Meanwhile, the mobile terminal may be set the first indicator 610 to be displayed only if user's movement is sensed. Moreover, the mobile terminal may be set the first indicator 610 to be displayed by a user's input signal (not shown).

The first indicator 610 may indicate a first activity amount 611 and a second activity amount 612. Here, the first activity amount 611 may indicate activity performed by a user during a unit time. For example, the unit time may correspond to 24 hours. Moreover, the second activity amount 612 may indicate an activity amount resulting from subtracting the first activity amount 611 from a goal activity amount when the goal activity amount is set to 100. Moreover, the first indicator 610 may indicate a real-time activity amount. Hence, depending on a level of movement of a user currently wearing the mobile terminal, the first indicator 610 can changes and display the first activity amount 611 by reflecting user's movement. Moreover, as the first activity amount 611 increases, the second activity amount 612 decreases.

Meanwhile, the mobile terminal may sense an input signal 620 to the first indicator 610. For example, the input signal 620 may include a short touch input, a long touch input, or the like. Since a size of the first indicator 610 is small, if the input signal 620 is sensed around the first indicator 610, the mobile terminal can determine it as the input signal to the first indicator 610.

In this case, the mobile terminal may send information on the sensed input signal 720 to an external device. Here, the external device may include various digital devices having displays. Moreover, assume that the mobile terminal is in the state of being paired with the external device. As shown in FIG. 6(b), the external device receives a signal from the mobile terminal and is able to display a detailed information 630 related to an activity amount on a display unit. In particular, the external device launches a healthcare application and is able to display the detailed information 630 related to the user's activity amount in the healthcare application. For example, the detailed information 630 may include total number of steps, total consumed calories, a traveled distance, etc.

Meanwhile, if sensing the input signal 620 to the first indicator 610, the mobile terminal launches an exercise related application and displays a detailed information related to an activity amount [not shown in FIG. 6]. Yet, since the mobile terminal has the display unit of which size is smaller than that of the external device, such detailed information can be displayed schematically unlike the detailed information 630 shown in FIG. 6(b).

Figure 7:
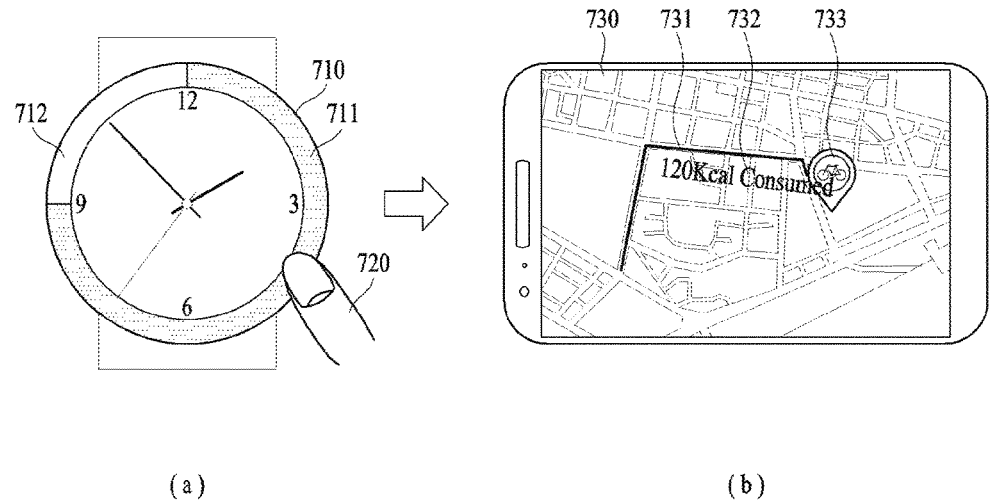
FIG. 7 is a diagram for one example of providing exercise information according to an input signal in a watch-type mobile terminal related to the present invention.

FIG. 7 is a diagram for one example of providing exercise information according to an input signal in a watch-type mobile terminal related to the present invention. In the embodiment of FIG. 7, description redundant with the former description with reference to FIG. 6 shall be omitted.

Referring to FIG. 7(a), a mobile terminal may display a first indicator 710 on a display unit. The mobile terminal may sense an input signal 720 to the first indicator 710. In this case, the mobile terminal may send information on the sensed input signal 720 to an external device.

Referring to FIG. 7(b), the external device receives a signal from the mobile terminal and may display a detailed information 730 related to an activity amount on the display unit. For example, the detailed information 730 may indicate information on user's movement on a map. Namely, the mobile terminal may display an information 731 on a user's movement location on the map, a calorie amount consumed according to activity, and a travel means 733. Meanwhile, the aforementioned information may include various informations as well as the detailed information 730 for example.

Meanwhile, if sensing the input signal 720 to the first indicator 710, the mobile terminal launches an exercise related application and displays detailed information related to activity [not shown in FIG. 7]. Yet, since the mobile terminal has the display unit of which size is smaller than that of the external device, unlike the detailed information 730 shown in FIG. 7(b), a map can be schematically displayed by being reduced.

Figure 8:
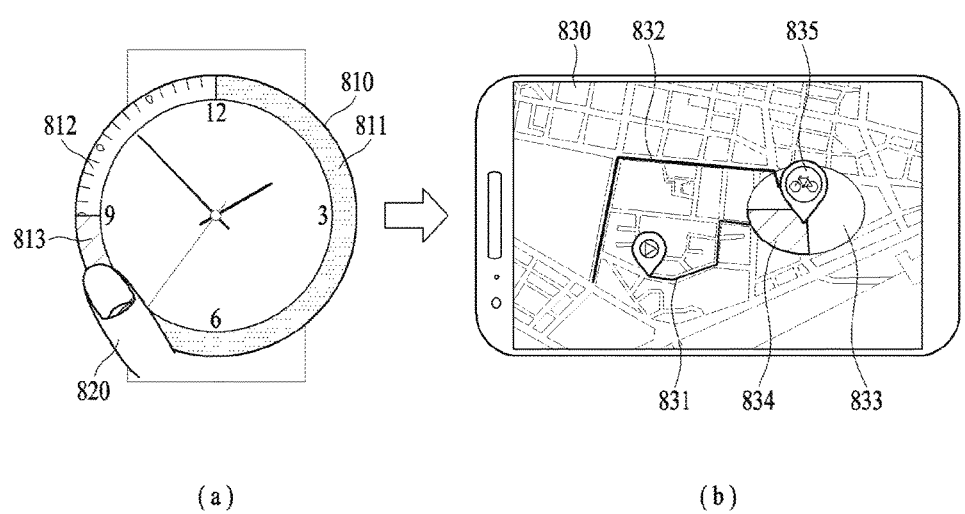
FIG. 8 is a diagram for one example of providing exercise information according to an input signal in a watch-type mobile terminal related to the present invention.

FIG. 8 is a diagram for one example of providing exercise information according to an input signal in a watch-type mobile terminal related to the present invention.

First of all, a mobile terminal may display a first indicator 810 on a display unit. In the embodiment of FIG. 8, the first indicator 810 may indicate a first activity amount 811, a second activity amount 812 and a third activity amount 813. Here, the first activity amount 811 may indicate a real-time activity amount performed by a user during a unit time. Moreover, the second activity amount 812 may indicate an activity amount resulting from subtracting the first activity amount 811 and the third activity amount from a goal activity amount when the goal activity amount is set to 100. Here, the third activity amount indicates a part that is not admitted as activity despite a user has moved. Namely, the third activity amount 813 may correspond to a deficient activity amount. For example, the third activity amount 813 may correspond to a part traveled by a user by taxi instead of walking.

Meanwhile, the mobile terminal may sense an input signal 820 to the first indicator 810. For example, as shown in FIG. 8(a), the mobile terminal may sense the input signal 820 to the third activity amount 813 in the first indicator 810. For example, the input signal 820 may include a short touch input, a long touch input, or the like.

In this case, the mobile terminal may send information on the sensed input signal 820 to an external device. As shown in FIG. 8(b), the external device receives a signal from the mobile terminal and is able to display a detailed information 830 related to a deficient activity amount on the display unit. For example, if a user travels a distance, which can be traveled by bicycle, by car, a deficient activity amount may be generated. Namely, in order to check the detailed information on the deficient activity amount 813 displayed on the mobile terminal, the user may apply a touch input to the display unit of the mobile terminal. In this case, the external device may display a section 832 traveled on a map by a user by car, an estimated travel route 831 in case of using a bicycle, an activity amount 834 in case of using a car, a recommended activity method 835 and the like. Through this, it is able to provide a guide so that a user can achieve an activity amount by changing a usual activity habit without preparing a separate exercise time.

Figure 9:
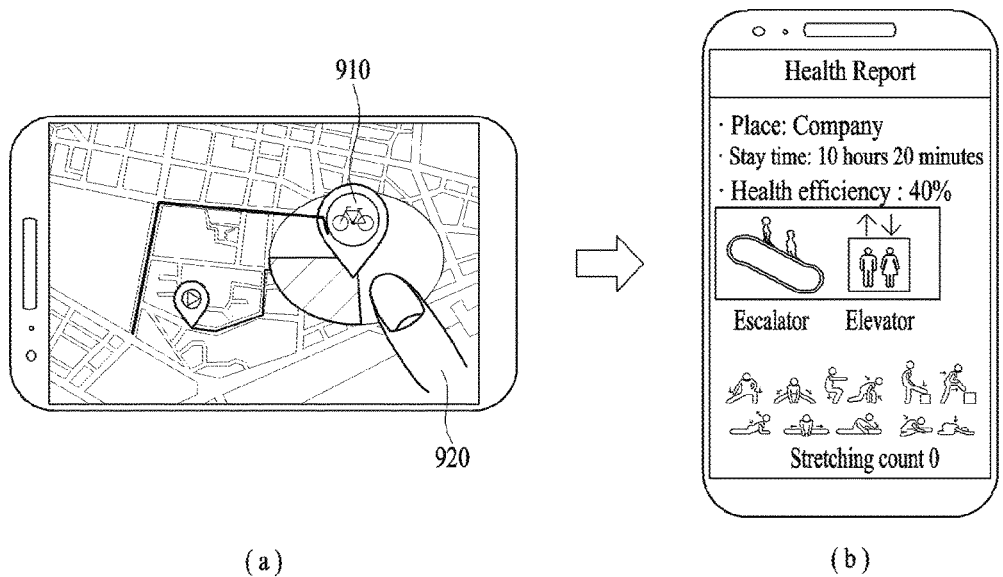
FIG. 9 is a diagram for one example of providing exercise information according to an input signal in a watch-type mobile terminal related to the present invention.

FIG. 9 is a diagram for one example of providing exercise information according to an input signal in a watch-type mobile terminal related to the present invention. In particular, FIG. 9 shows an embodiment of providing a health guide if a user stays in a specific area for a long time in the embodiment of FIG. 8.

First of all, referring to FIG. 9(a), an external device can display detailed information on user's activity amount. In this case, in comparison with the detailed information 830 shown in FIG. 8(b), the mobile terminal can enlarge and display a graph indicating the activity amount shown in FIG. 9(a). Namely, the mobile terminal can enlarge the graph indicating the activity amount 910 in proportion to a user stay time.

In this case, the external device can sense an input signal 920. The input signal 920 may include a short touch input, a long touch input and the like for example. In this case, as shown in FIG. 9(b), the external device can display a health report 930. Here, the health report 930 may provide a user located place, a stay time, a health efficiency, a user's activity amount at a user located place, and the like. Through this, a user can check health efficiency in case of a long stay in one place and an exercise method for raising health efficiency and the like.

Figure 10:
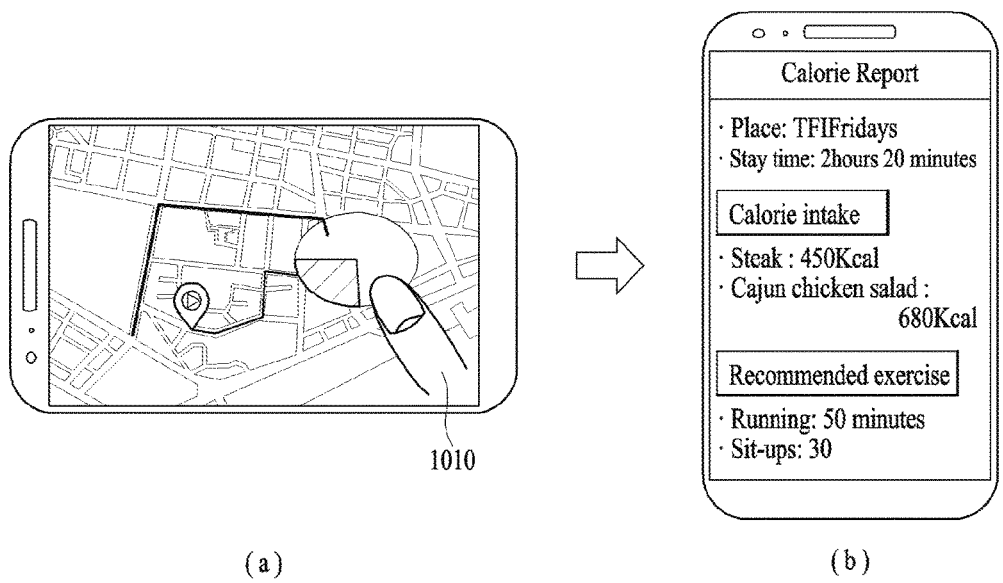
FIG. 10 is a diagram for one example of providing exercise information according to an input signal in a watch-type mobile terminal related to the present invention.

FIG. 10 is a diagram for one example of providing exercise information according to an input signal in a watch-type mobile terminal related to the present invention.

In particular, if a user stays in a restaurant in the embodiment of FIG. 8, FIG. 10 shows an embodiment of providing a user with a health guide. Here, a mobile terminal or an external device can provide the health guide based on a user-paid card bill, a receipt, a menu of a located restaurant and the like. In FIG. 10, description redundant with the former description of the embodiment of FIG. 9 shall be omitted.

First of all, referring to FIG. 10(a), a mobile terminal or an external device can sense an input signal 1020 to a graph indicating an activity amount 1010. In this case, as shown in FIG. 10(b), the external device can display a calorie report 1030. Here, the calorie report can provide a user-located restaurant, a stay time, a calorie intake based on a user-ordered menu, a corresponding recommended exercise and the like.

Figure 11:
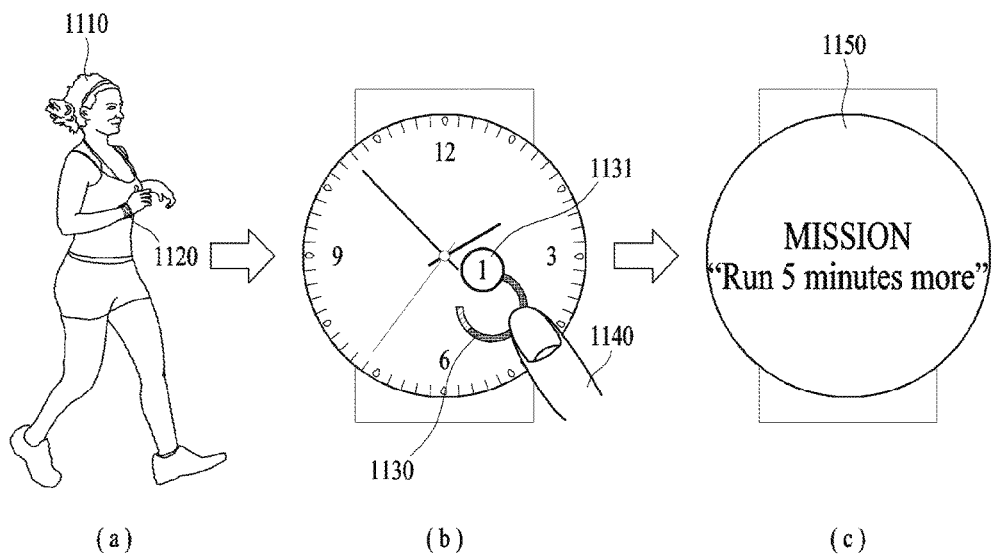
FIG. 11 is a diagram for one example of providing an exercise guide based on user's movement in a watch-type mobile terminal of the present invention.

FIG. 11 is a diagram for one example of providing an exercise guide based on user's movement in a watch-type mobile terminal of the present invention.

First of all, a mobile terminal can sense a movement of a user 1110. In particular, as shown in FIG. 11(a), the user 1110 may correspond to 'walking' in a state of wearing the mobile terminal 1120.

Based on the sensed movement of the user, the mobile terminal can determine whether the user is in taking daily activity or exercise. For example, in the embodiment of FIG. 11(a), the mobile terminal can sense that the user is walking. Moreover, for instance, regarding the user's movement, the mobile terminal can sense that the user is walking based on the aforementioned exercise information. Here, the exercise information may correspond to at least one of a movement of the mobile terminal, a heart rate of the user wearing the mobile terminal, a moving speed of the mobile terminal, a travel distance of the mobile terminal, an altitude of the mobile terminal, an inclination of the mobile terminal, and an acceleration of the mobile terminal.

In this case, the mobile terminal can display a first indicator 1130 indicating a real-time activity amount on the display unit. In the embodiment of FIG. 11(b), the first indicator 1130 may be displayed within a watch. In addition to the first indicator 1130, the mobile terminal may display a mission indicator 1131. For example, based on the sensed exercise information, if a user stops for a while or a moving speed gets slow, the mobile terminal can display the mission indicator 1131.

Here, the mission indicator 1131 may correspond to an indicator additionally indicating a method for increasing an activity amount or an exercise amount if a user is doing daily activity. Moreover, the numeral displayed on the mission indicator 1131 may correspond to the number of methods for increasing an activity amount or an exercise amount. In the embodiment of FIG. 11(b), the mobile terminal may provide a user with a single method for increasing an activity amount or an exercise amount. Meanwhile, after the mission indicator 1131 has been displayed, if a user's input signal is not sensed within a preset time, the mission indicator 1131 may be removed from the first indicator 1130.

Referring to FIG. 11(b), the mobile terminal can sense an input signal 1140 to the first indicator. Here, the input signal 1140 may correspond to a short or long touch input. In doing so, the mobile terminal may display a content 1150 corresponding to the mission indicator on the display unit. For example, as shown in FIG. 11(c), the mobile terminal may display 'MISSION: Run 5 minutes more'. For example, now shown in FIG. 11, if sensing that a user is using public transportation, the mobile terminal may display 'Get off a stop early and walk'.

In this case, not shown in FIG. 11, after the content 1150 corresponding to the mission indicator has been displayed by overlaying a watch screen, if a user's additional input signal is sensed or a preset time expires, the watch screen may be displayed again.

Figure 12:
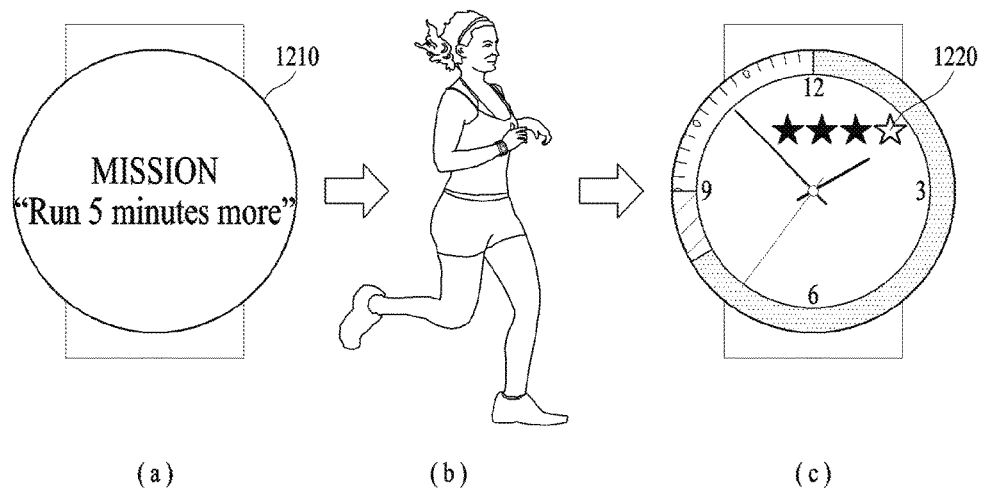
FIG. 12 is a diagram for one example of providing an exercise guide based on user's movement in a watch-type mobile terminal of the present invention.

FIG. 12 is a diagram for one example of providing an exercise guide based on user's movement in a watch-type mobile terminal of the present invention. In particular, FIG. 12 shows compensation provided to a user if the mission provided in the embodiment of FIG. 11 is accomplished.

In continuation with FIG. 11, as shown in FIG. 12(a), the mobile terminal can display a mission content 1210 on the display unit. In this case, the mobile terminal can sense a user's movement. In particular, as shown in FIG. 12(b), based on the user's exercise information, the mobile terminal can sense that the user is in running. And, the running may correspond not to a daily activity but to an exercise.

If the user accomplishes the mission, the mobile terminal may display a compensation indicator 1220. For example, the compensation indicator 1220 may be configured in various forms. Each time a mission is accomplished, the mobile terminal may change a content of the compensation indicator 1220. In the embodiment of FIG. 12(c), after the user has already accomplished 3 missions, while 3 star-type indicators are displayed, since another mission is accomplished in addition, a single star is added. The compensation indicator 1220 shall be described again with reference to FIG. 13.

Figure 13:
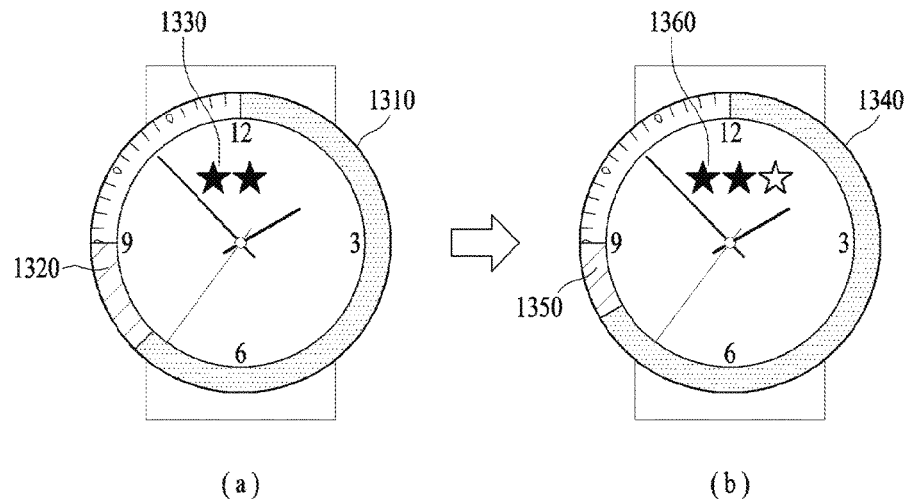
FIG. 13 is a diagram for one example of displaying a compensation indicator based on a real-time activity amount in a watch-type mobile terminal of the present invention.

FIG. 13 is a diagram for one example of displaying a compensation indicator based on a real-time activity amount in a watch-type mobile terminal of the present invention.

As described above, a first indicator 1310 may indicate a current activity amount over a goal activity amount. Hence, a motivation of fulfilling 100% of a goal can be given to a user by the first indicator 1310. Meanwhile, while displaying the first indicator 1310, the mobile terminal can additionally display a compensation indicator 1330. In order to maintain health by increasing a user's activity amount, after the mobile terminal have given a mission to a user, if the user accomplishes the mission successfully, the compensation indicator 1330 can be displayed.

In the embodiment of FIG. 13(a), if the user accomplishes the mission successfully, the mobile terminal can display the compensation indicator 1330 on the display unit. Here, as described in FIG. 11 and FIG. 12, the mission may correspond to a method for complementing a physical strength additionally like 'run 5 minutes more' based on a current state. For example, the compensation indicator 1330 may be displayed in shape of star, by which the shape is non-limited.

The embodiment of FIG. 13(a) may correspond to a case that the user has accomplished 2 of a plurality of given missions successfully.

Meanwhile, beside the given mission, the mobile terminal can additionally sense a user's daily activity amount. In particular, as shown in FIG. 13(b), a real-time activity amount 1340 increases more than the real-time activity amount 1310 of FIG. 13(a), and a deficient activity amount 1350 may correspond to a state smaller than the deficient activity amount 1320 of FIG. 13(a). This may correspond to a case that a deficient activity amount is reduced as a user changes a previous life pattern.

In this case, the mobile terminal may provide the user with additional compensation. In particular, the mobile terminal may display an additional compensation indicator 1360 in addition to the compensation indicator 1330. Through this, the user can recognize that the user's activity amount is helpful to maintain health and feel a sense of achievement.

Figure 14:
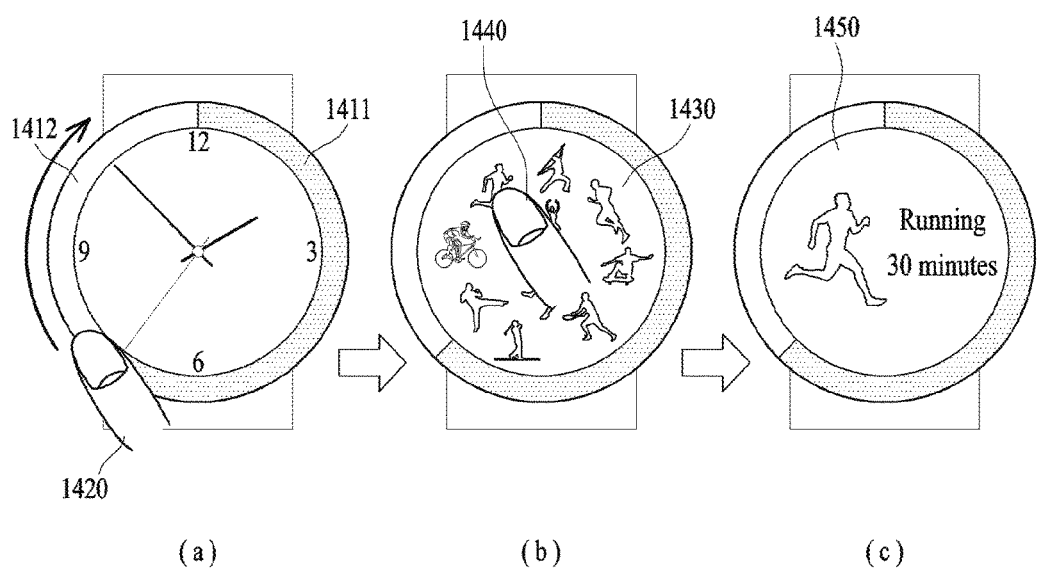
FIG. 14 is a diagram for one example of providing exercise information according to an input signal in a watch-type mobile terminal related to the present invention.

FIG. 14 is a diagram for one example of providing exercise information according to an input signal in a watch-type mobile terminal related to the present invention. In particular, FIG. 14 shows that if an activity amount fails to reach a goal activity amount, a guide is provided to reach the goal activity amount.

Referring to FIG. 14(a), if a user is performing daily activity, a mobile terminal can display a first indicator 1410. The first indicator 1410 may include a first activity amount 1411 indicating a current activity amount and a second activity amount 1412 indicating a difference between a goal activity amount and the current activity amount. In doing so, the mobile terminal may sense a first input 1420 to the first activity amount 1411. In particular, as shown in FIG. 14(a), the mobile terminal can sense a first input signal 1420 to an end point of the first activity amount 1411. Here, the input signal 1420 may correspond to a drag touch input or a flicking touch input. For example, the input signal 1420 may correspond to a touch drag input ending at a start point of the first activity amount 1411 by starting from an end point of the first activity amount 1411. This may correspond to an input applied to check a method for a user to fulfill a goal activity amount.

In this case, as shown in FIG. 14(b), the mobile terminal may display a first exercise guide 1430. The first exercise guide 1430 may display various exercises recommended to a user based on a current activity amount. For example, as shown in FIG. 14(b), the first exercise guide 1430 may be represented as an icon representing each exercise. Moreover, for example, the first exercise guide 1430 may be represented as a text icon.

Subsequently, the mobile terminal may sense a second input signal 1440 to the exercise guide 1430. For example, the second input signal 1440 may correspond to a short or long touch input. In the embodiment of FIG. 14(b), the second input signal 1440 may correspond to a signal for selecting a running from the first exercise guide 1440.

In this case, the mobile terminal may display a second exercise guide 1450 in response to the second input signal 1440. In particular, as shown in FIG. 14(c), in response to the second input signal 1440, the mobile terminal may provide a detailed guide for the exercise selected by the second input signal. For example, the second exercise guide 1450 can display an exercise type and an exercise time.

Figure 15:
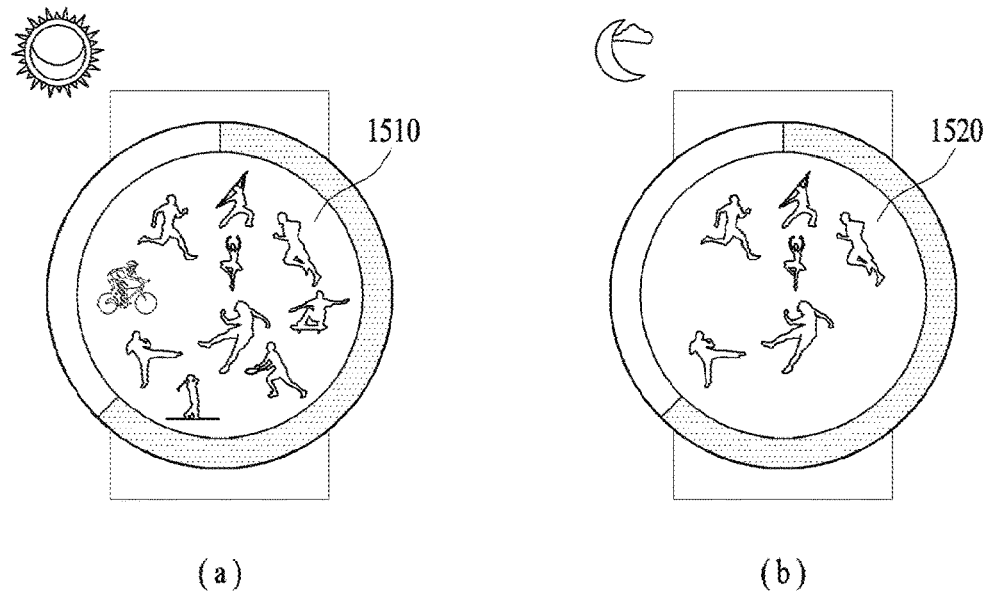
FIG. 15 is a diagram for one example of providing exercise information in a watch-type mobile terminal related to the present invention.

FIG. 15 is a diagram for one example of providing exercise information in a watch-type mobile terminal related to the present invention. In particular, FIG. 15 shows an embodiment of providing a type of an exercise contained in the aforementioned exercise guide differently on the basis of an exercise time.

First of all, FIG. 15(a) shows a case that the first input signal mentioned in FIG. 14 is sensed in daytime. In this case, as recommended exercises, the mobile terminal may display exercises good to be taken in daytime on an exercise guide 1510. For example, the exercises good to be taken in daytime may include running, golf, ski, snowboard, baseball and the like. Moreover, FIG. 15(b) shows a case that the first input signal mentioned in FIG. 14 is sensed in night-time. In this case, as recommended exercises, the mobile terminal may display exercises good to be taken in night-time on an exercise guide 1520.

Meanwhile, if the first input signal mentioned in FIG. 14 corresponds to business hours in which a user is busy, the mobile terminal may display an exercise capable of consuming calories quickly on the exercise guide [not shown in FIG. 15]. Namely, if sensing an input signal, the mobile terminal can provide types of exercises included in the exercise guide differently based on various user-involved situations.

Figure 16:
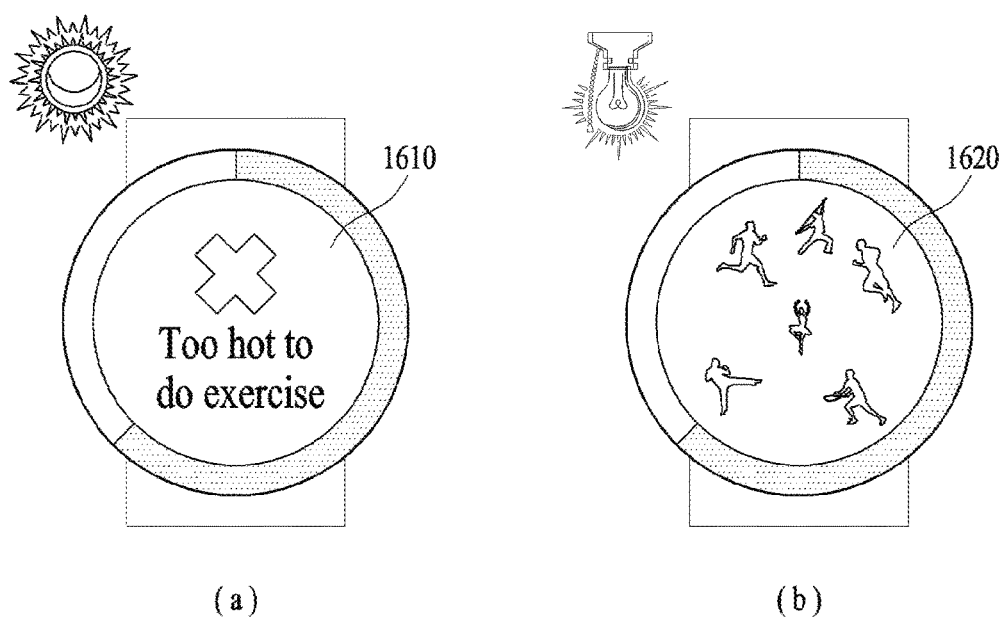
FIG. 16 is a diagram for one example of providing exercise information in a watch-type mobile terminal related to the present invention.

FIG. 16 is a diagram for one example of providing exercise information in a watch-type mobile terminal related to the present invention. In particular, FIG. 16 shows an embodiment of providing a type of an exercise contained in the aforementioned exercise guide differently on the basis of an exercise place.

First of all, FIG. 16(a) shows a case that the first input signal mentioned in FIG. 14 is sensed in an outdoor place. In case of the outdoor place, the mobile terminal may sense additional environment information such as temperature and humidity. For example, when the first input signal is sensed, the temperature may correspond to about 30 degrees. In this case, the mobile terminal does not recommend an exercise but may display a rest recommending content on an exercise guide 1610. Moreover, FIG. 16(b) shows a case that the input signal mentioned in FIG. 14 is sensed in an indoor place. In this case, as recommended exercises, the mobile terminal can display exercises good to be taken indoors on an exercise guide 1620.

Figure 17:
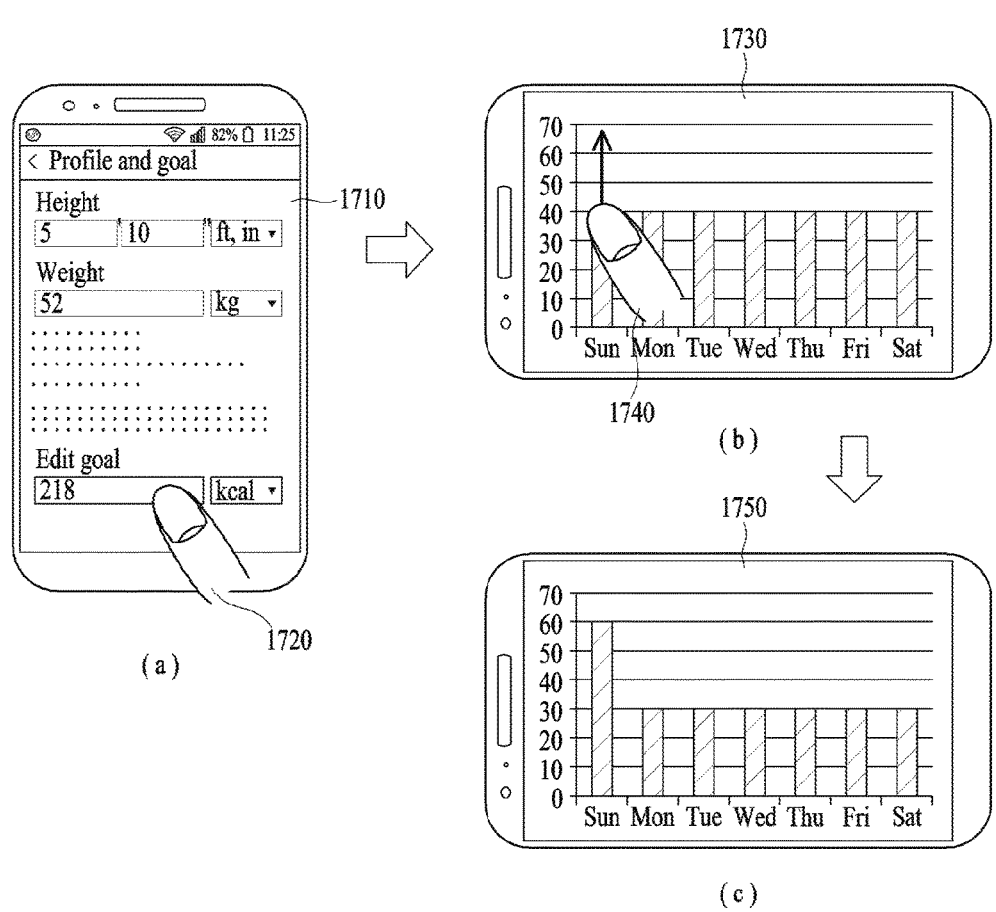
FIG. 17 is a diagram for one example of setting an exercise goal in a watch-type mobile terminal related to the present invention.

FIG. 17 is a diagram for one example of setting an exercise goal in a watch-type mobile terminal related to the present invention.

In particular, FIG. 17 shows that in an external device paired with a mobile terminal, a user's exercise goal is set according to an input signal. The embodiment of FIG. 17 corresponds to a case that a user currently wearing a mobile terminal sets an exercise goal in a state of not doing daily activity or exercise.

Referring to FIG. 17(a), an external device can sense a first input signal 1720 while an exercise application 1710 is running. For example, the first input signal 1720 may correspond to a short or long touch input. And, the first input signal 1720 may correspond to an input signal for setting an exercise goal on the exercise application 1710.

In this case, as shown in FIG. 17(b), the external device can display a weekly goal 1730. Meanwhile, assume that the exercise application can record a user's exercise pattern and set a next week goal automatically according to the user's exercise pattern.

For one example, in case of a user having a pattern of taking exercise 7 days a week, a goal on the exercise application can be set to consuming the same amount of calories every day. For another example, in case of a user capable of taking exercise not on weekdays but on weekend, a goal on the exercise application can be set to consuming a considerable amount of calories on weekend by lowering a goal of calories to be consumed on weekdays. For further example, in case of a user capable of taking exercise on Monday/Wednesday/Friday only, a goal on the exercise application can be set to consuming a considerable amount of calories to be consumed on Monday/Wednesday/Friday.

The case of the embodiment of FIG. 17(b) may correspond to an exercise goal set for a user having a pattern of taking exercise 7 days a week. In this case, the external device may sense a second input signal 1740. For example, the second input signal 1740 may correspond to a drag touch input. And, the second input signal 1740 shown in FIG. 17(b) may correspond to a drag touch input for increasing a goal exercise amount of Sunday. In this case, as shown in FIG. 17(c), the exercise goal of Sunday increases, whereby exercise goals of the rest of the days of the week may decrease. Namely, through the embodiment of FIG. 17, although an exercise goal has been set already, it can be changed in detail according to a user's input and a user's pattern.

Figure 18:
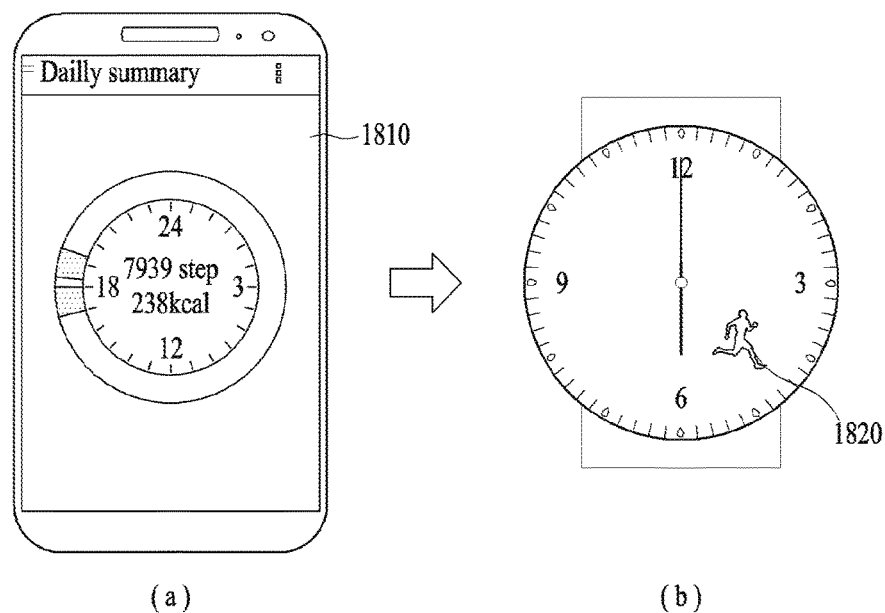
FIG. 18 is a diagram for one example of providing an exercise alarm in a watch-type mobile terminal related to the present invention.

FIG. 18 is a diagram for one example of providing an exercise alarm in a watch-type mobile terminal related to the present invention.

In particular, FIG. 18 shows an embodiment of providing a user with an alarm at a preset time. In the embodiment of FIG. 18, the preset time may correspond to a time in which a user can take exercise based on an exercise record.

In the embodiment of FIG. 18(a), an exercise record 1810 is recorded as a user mainly takes exercise 6 P.M. In this case, as shown in FIG. 18(b), a mobile terminal can display an alarm indicator 1820 on a watch screen. Here, the alarm indicator 1820 may be displayed in various forms. For example, as shown in FIG. 18(b), the alarm indicator 1820 can display an image indicating a recommended exercise. Namely, the mobile terminal provides a notification at a time in which a user can take exercise, thereby leading the user to take exercise.

Meanwhile, considering an exercise record, if an exercise record of the very day is less than that of a previous day, the mobile terminal may display an alarm indicator on the watch screen [not shown in FIG. 18]. For example, the mobile terminal displays an alarm indicator at a user's quitting time, thereby leading the user to run by getting off a stop early.

Figure 19:
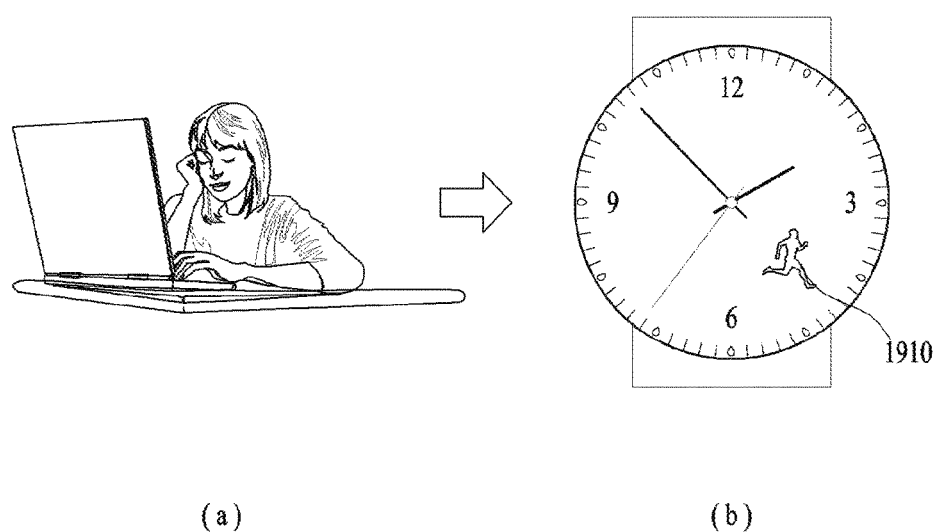
FIG. 19 is a diagram for one example of providing an exercise alarm in a watch-type mobile terminal related to the present invention.

FIG. 19 is a diagram for one example of providing an exercise alarm in a watch-type mobile terminal related to the present invention.

In particular, FIG. 19 shows an embodiment of providing an alarm to a user at a preset time. In the embodiment of FIG. 19, the preset time may correspond to a time in which an exercise is necessary for a user.

Referring to FIG. 19(a), a user may be sleepy after a lunch time. In this case, a mobile terminal can display an alarm indicator 1910 on a watch screen in consideration of user's movement, time and the like. Here, the alarm indicator 1920 can display an image indicating a recommended exercise. In the embodiment of FIG. 19(b), the alarm indicator 1910 can display an image indicating a running exercise. Namely, the mobile terminal provides a notification at a time in which a user needs exercise, thereby leading the user to take exercise.

Meanwhile, although not shown in FIG. 19, if a user is a student or an office worker and studies or works on a desk for 50 minutes, 10-minute stretching may be necessary. In this case, if it is determined that the user has studied or worked for 50 minutes in consideration of user's movement, location, time and the like, the mobile terminal can display an alarm indicator on a watch screen.

Meanwhile, although not shown in FIG. 19, if a user takes exercise frequently, a recovery period may be required according to strength of exercise. For example, the recovery period may variously range from 2~3 hours to a week depending on strength of the exercise taken by the user. Namely, if a user takes exercise before a body is recovered, physical strength may be further reduced. Moreover, if exercise is not taken too long, since physical strength is reduced, it may be difficult to recover the physical strength despite taking exercise. Hence, a user needs to take exercise without taking a break too long.

In this case, the mobile terminal senses the user's exercise strength and is then able to display an alarm indicator on the watch screen after expiration of the recovery period. For example, if 2-day recovery period expires after doing exercise, the mobile terminal displays an alarm indicator on the watch screen on $3^{rd}$ day, thereby leading a user to take exercise.

Figure 20:
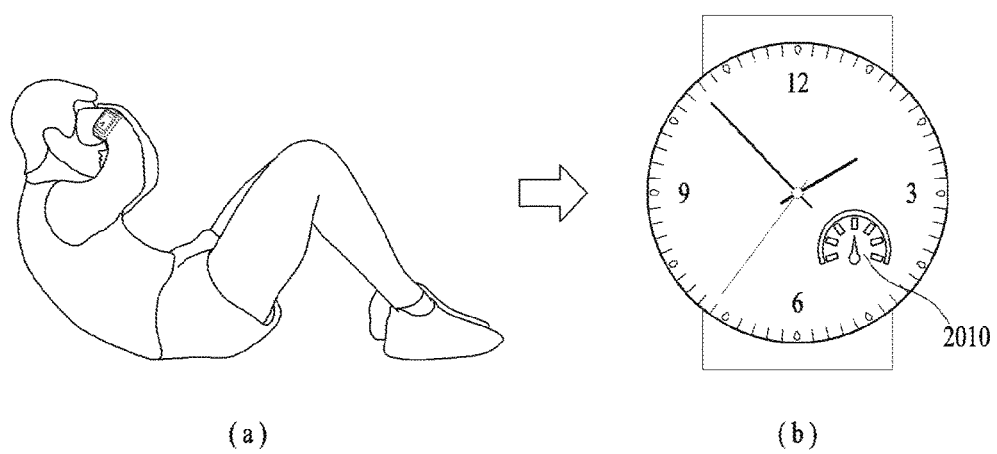
FIG. 20 is a diagram for one example of displaying exercise efficiency in a watch-type mobile terminal related to the present invention.

FIG. 20 is a diagram for one example of displaying exercise efficiency in a watch-type mobile terminal related to the present invention.

First of all, a mobile terminal can sense user's movement. In particular, as shown in FIG. 20(a), the user may be doing sit-ups while wearing the mobile terminal.

Moreover, based on the sensed movement of the user, the mobile terminal can determine whether the user is doing daily life or exercise. For example, in the example of FIG. 20(a), as the user is doing sit-ups, the mobile terminal may determine that the user is doing exercise. For example, regarding user's movement, it is able to sense that the user is doing walking based on the aforementioned exercise information. Here, as described above, the exercise information may correspond to at least one of a movement of the mobile terminal, a heart rate of the user wearing the mobile terminal, a moving speed of the mobile terminal, a travel distance of the mobile terminal, an altitude of the mobile terminal, an inclination of the mobile terminal, and an acceleration of the mobile terminal.

In this case, the mobile terminal may determine whether it corresponds to 'after end of exercise'. For example, if it corresponds to 'after end of exercise', it may correspond to a case that there is no movement of a user for a preset time. Moreover, a case that it corresponds to 'after end of exercise' may correspond to a case that user's movement rapidly decreases. Moreover, if exercise is ended, the mobile terminal can display a second indicator 2010 indicating exercise efficiency on the display unit. For example, the mobile terminal can display the second indicator 2010 within the watch screen. Moreover, for example, the second indicator 2010 can be displayed based on the exercise taken shortly before by the user.

Regarding this, exercise efficiency can be determined with reference to exercise strength of the same age group. For example, the exercise strength may include maximum oxygen intake amount, straightness, sit-up count, side-step count, etc. Moreover, based on user's heart rate sensed in the course of exercise, it is able to perform physical strength comparison when other persons of the same age group are taking a specific exercise. For example, the specific exercise may correspond to sit-up, one-leg standing with closed eyes, jumping up and down on a chair, or 100 m running.

Meanwhile, the mobile terminal converts exercise efficiency into a grade and displays it on the second indicator 2010. For example, the exercise efficiency can be classified into first to fifth grades and an average of the exercise efficiency may correspond to the third grade. A highest exercise efficiency state may correspond to the first grade and a lowest exercise efficiency state may correspond to the fifth grade. In the embodiment of FIG. 20(b), user's exercise efficiency may correspond to the third grade. Through this, the user can be intuitively and directly aware of the exercise efficiency of the exercise taken shortly before by the user.

Figure 21:
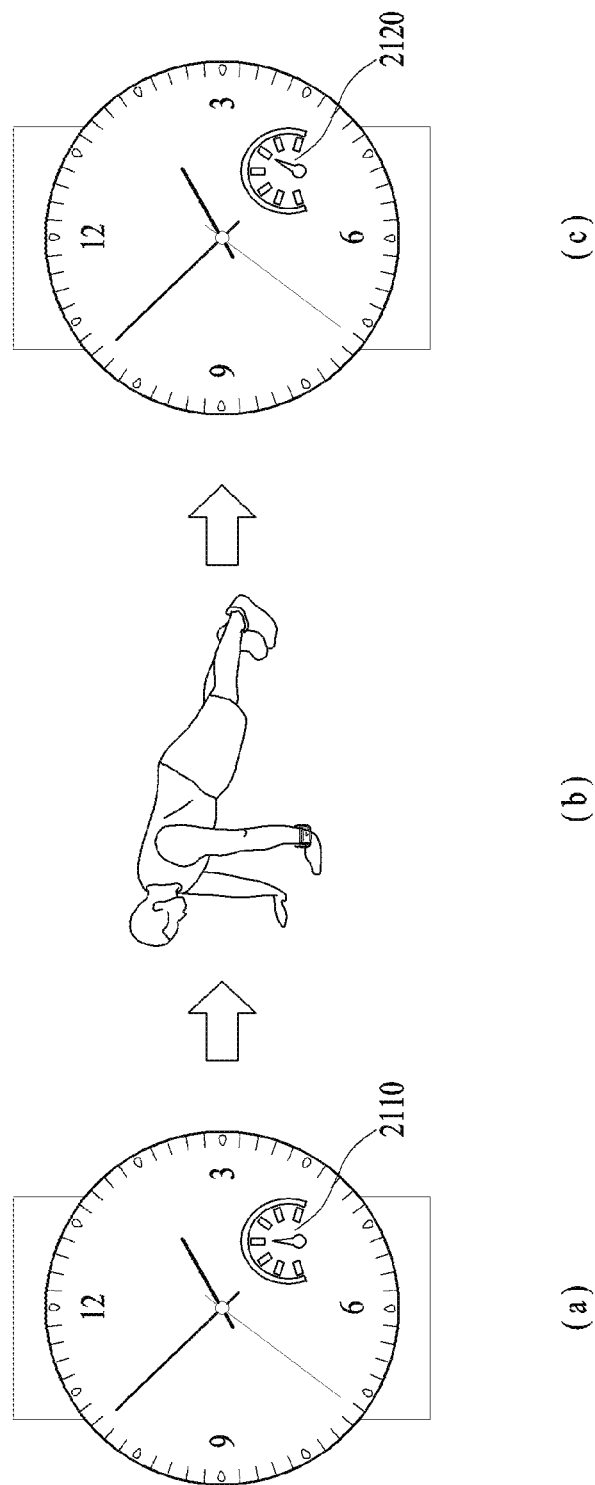
FIG. 21 is a diagram for one example of displaying exercise efficiency in a watch-type mobile terminal related to the present invention.

FIG. 21 is a diagram for one example of displaying exercise efficiency in a watch-type mobile terminal related to the present invention. In particular, FIG. 21 shows exercise efficiency when additional exercise is further taken after the end of the exercise of FIG. 20.

In continuation with FIG. 20, the mobile terminal can represent user's exercise efficiency as the third grade on a second indicator 2110. In this case, the user checks the user's exercise efficiency and may be motivated to further raise the exercise efficiency. Hence, the user wearing the mobile terminal may take exercise additionally. For example, as shown in FIG. 21(b), the mobile terminal wearing user can do sit-ups 10 times additionally.

In this case, as described in FIG. 20, the mobile terminal senses user's movement and is then able to determine whether the user's sensed movement is exercising. In the embodiment of FIG. 21(b), the user may correspond to a state of having done the exercise of the sit-up. Moreover, if the exercise corresponds to an exercise ended state, the mobile terminal can display a second indicator 2120 indicating exercise efficiency on the display unit. In doing so, the mobile terminal may display the second indicator 2120 indicating exercise efficiency changed based on an exercise additionally taken by the user. As shown in FIG. 21(c), due to the user's additional exercise, the mobile terminal can display the second indicator 210 by changing the exercise efficiency into the second grade from the third grade. Through this, the user can be motivated to take exercise.

Figure 22:
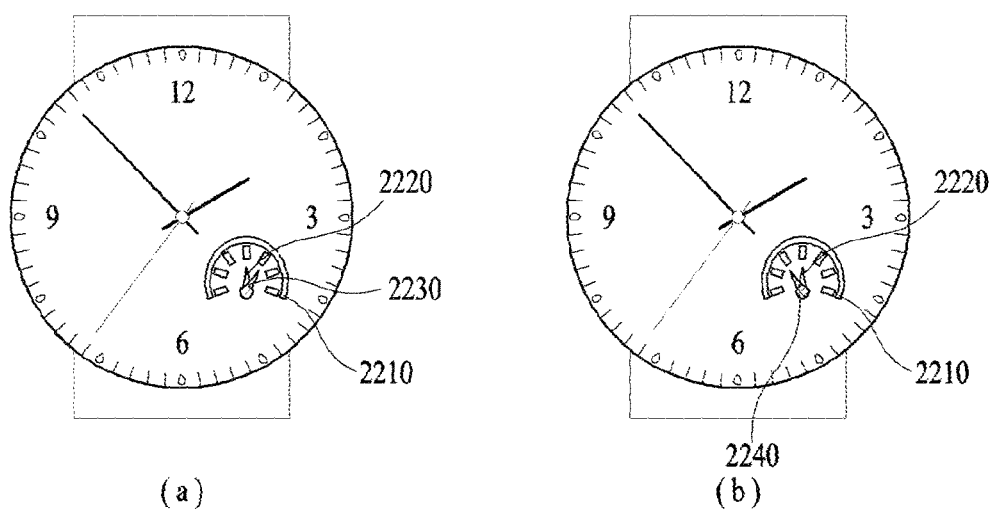
FIG. 22 is a diagram for one example of a second indicator displaying exercise efficiency in a watch-type mobile terminal related to the present invention.

FIG. 22 is a diagram for one example of a second indicator displaying exercise efficiency in a watch-type mobile terminal related to the present invention.

A second indicator 2210 may include an average line 2220 and a line 2230 indicating user's exercise efficiency. The average line indicates an average of exercise efficiency and can be set by various references. For example, the average line 2220 may correspond to user's average exercise efficiency based on user's past physical strength and exercise. Moreover, for example, the average line 2220 may correspond to average exercise efficiency based on standard physical strength of person of the same age group. Moreover, for example, the average line 2220 may be determined on the basis of user's exercise goal. Here, the user's exercise goal may correspond to an exercise goal value previously set by a user for diet or physical strength enhancement.

Based on user's past physical strength and exercise, if the average line 2220 is set, the average line 2220 may be updated by periods of a preset term or set to be updated with reference to a specific day. For example, the specific data may correspond to a date on which intensive exercise is taken specially. Moreover, the specific day may correspond to a date on which exercise is started. Moreover, the specific day may correspond to the same date that was a week, a month or a year ago.

Referring to FIG. 22(a), the second indicator 2210 is displayed within a watch screen and may include an average line 2220 and a line 2230 indicating exercise efficiency. Here, the line 2230 indicating user's exercise efficiency may correspond to a case of being higher than the average line 2220. This may correspond to a case that the exercise taken by the user has efficiency higher than that of the previously taken exercise. Moreover, for example, it may correspond to a case that the exercise taken by the user has average exercise efficiency higher than that of the same age group. Moreover, for example, it may correspond to a case that the exercise taken by the user exceeds a user's exercise goal.

Referring to FIG. 22(b), the second indicator 2210 is displayed within a watch screen and may include an average line 2220 and a line 2240 indicating exercise efficiency. Here, the line 2240 indicating user's exercise efficiency may correspond to a case of being lower than the average line 2220. This may correspond to a case that the exercise taken by the user has efficiency lower than that of the previously taken exercise. Moreover, for example, it may correspond to a case that the exercise taken by the user has average exercise efficiency lower than that of the same age group. Moreover, for example, it may correspond to a case that the exercise taken by the user fails to exceed a user's exercise goal.

Namely, through the embodiment of FIG. 22, the user can easily recognize efficiency of exercise taken by the user in comparison with an average exercise efficiency.

Figure 23:
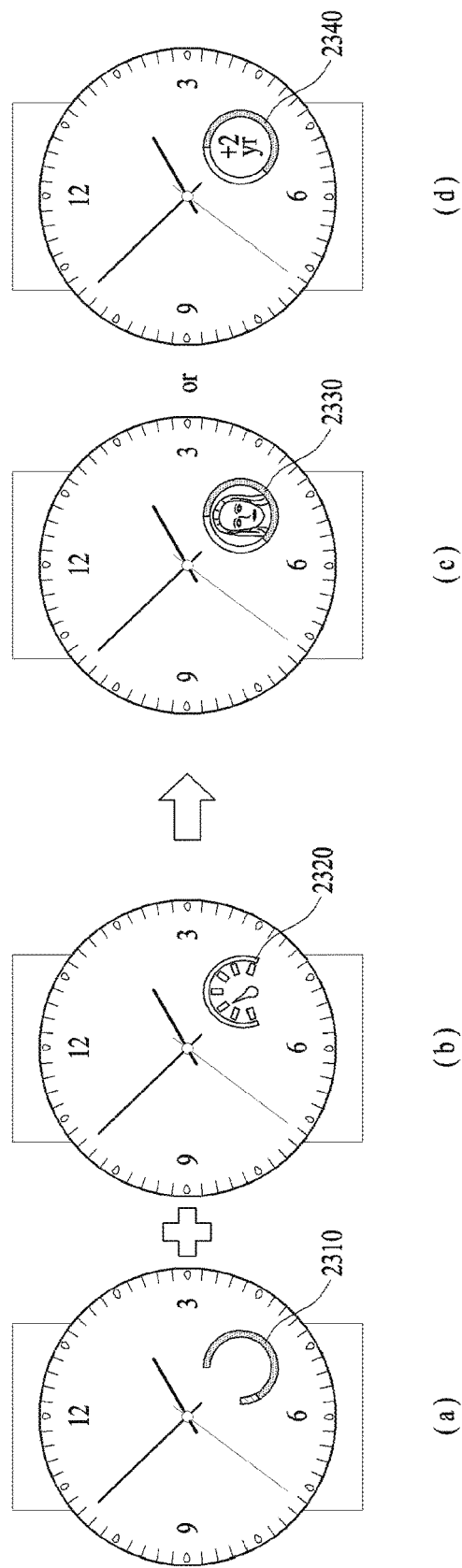
FIG. 23 is a diagram for one example of a third indicator indicating a physical age in a watch-type mobile terminal related to the present invention.

FIG. 23 is a diagram for one example of a third indicator indicating a physical age in a watch-type mobile terminal related to the present invention. In particular, FIG. 23 shows an embodiment of providing a third indicator displayed on a watch screen each time a preset period expires.

As described above, a first indicator 2310 shown in FIG. 23(a) may indicate a user's activity amount and a second indicator 2320 shown in FIG. 23(b) may indicate user's exercise efficiency after end of exercise. Moreover, a mobile terminal can display a third indicator 2230/2240 indicating a user's physical age on a watch screen based on the first and second indicators 2310 and 2320. Namely, the mobile terminal determines a user's physical age in consideration of activities in user's daily life and user's overall movements including a state of an exercise taken by the user, and is then able to display it on a display unit.

The third indicator 2230/2240 may be displayed on the watch screen in various forms. For example, as shown in FIG. 23(c), the third indicator 2230 can indicate a physical age using a human face and a background color. Here, the human face may be used in a manner of being extracted from a user's photo stored in the mobile terminal or an external device. This shall be described again with reference to FIG. 24 later. Moreover, the background color may be determined based on a physical strength index determined on the basis of exercise efficiency. For example, green may indicate a good physical strength state, yellow may indicate a slightly bad physical strength state, and red may indicate a very bad physical strength state.

For another example, as shown in FIG. 23(d), the third indicator 2240 can indicate a physical age as a text in comparison with a user's actual age. For example, if a user's physical age is determined as 2 years older than an actual age, '+2 yr' may be displayed on the third indicator 2340. Here, the third indicator 2340 may indicate a user's physical strength index using a background color. Through the third indicator 2340, the user can be intuitively aware of the physical age of the user.

Meanwhile, when exercise information is not sensed, a case of displaying the third indicator 2230/2240 is described in the present embodiment. Yet, although the exercise information is sensed, as a preset period expires, the third indicator 2230/2240 may be displayed on the watch screen simultaneously with or separately from the first indicator or the second indicator.

FIG. 24 is a diagram for one example of a third indicator indicating a physical age in a watch-type mobile terminal related to the present invention. In particular, FIG. 24 shows a method of expressing a human face included in the aforementioned third indicator in FIG. 23.

As described in FIG. 23, the mobile terminal can represent a human face on a third indicator 2410. Through the human face, a user can predict a physical age of the user. In doing so, in order to provide the user with the maximum motivation for exercise or activity, a photo of the user can be displayed on the third indicator 2410.

For example, if a user is in thirties, a photo of the user in thirties may be prepared in a memory of a user's mobile terminal or an external device or an external memory. Yet, a future photo after forties may not be prepared in the memory of the mobile terminal or the external device and the external memory as well as photos in user's tens or twenties. Hence, in case of using a user's photo, a user's face can be changed to match various age groups on a separate photo correction program.

Referring to FIG. 24(b), with reference to a user's actual face, through a photo correction program, a user face can be changed into a child photo and an old man photo. The mobile terminal can display a changed photo on the third indicator 2410 to match the user's physical age. For example, as a user has taken exercise hard, a physical age gets younger, the mobile terminal can display a photo, which is located on the left side with reference to a user's actual photo 2420, on the third indicator 2410. For another example, as a user has not taken exercise, a physical age gets older, the mobile terminal can display a photo, which is located on the right side with reference to the user's actual photo 2420, on the third indicator 2410.

Meanwhile, as a user has done appropriate activity and exercise to match an age group of the user, if a physical age matches the age group of the user, the user's actual face 2420 may be displayed on the third indicator 2410 [not shown in FIG. 24]. In this case, if the same face of the user is displayed for a long term, user's interest may be lowered. Hence, if there is a photo recently taken by the user, the mobile terminal can automatically update the third indicator 2410 with a user's face appearing in the recent photo. Moreover, since there may be a photo the user does not like among photos stored in a user's gallery, the mobile terminal may automatically update a user's face by prioritizing photos uploaded to SNS and the like by the user.

Figure 25:
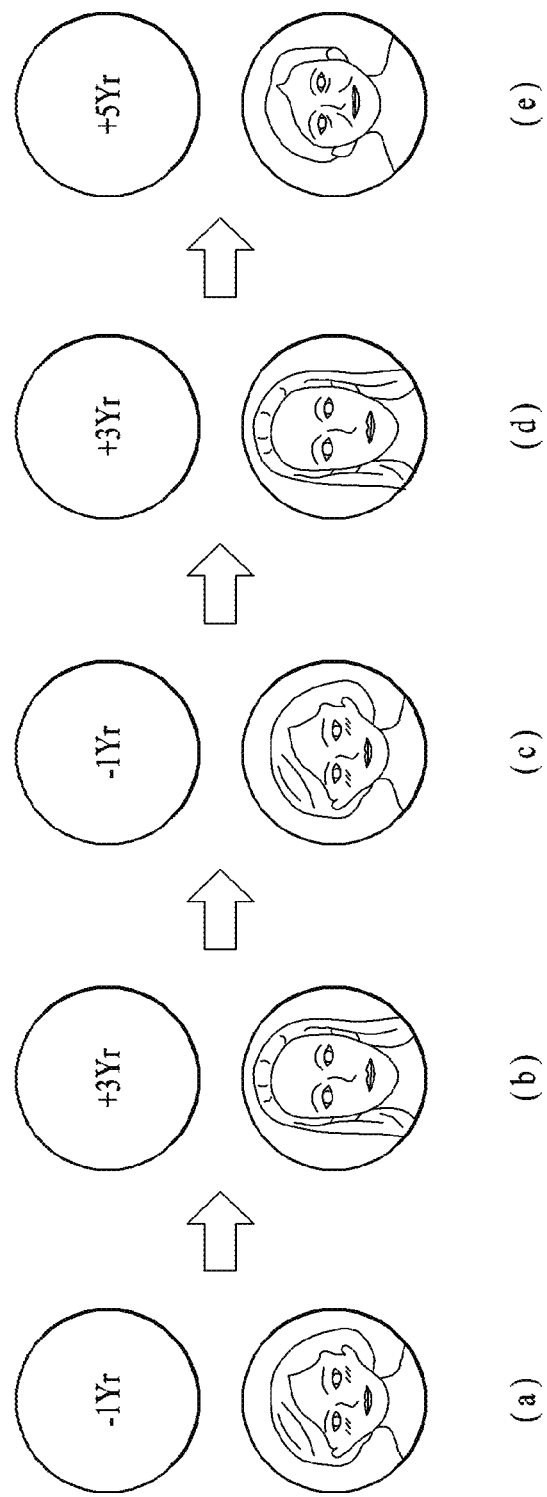
FIG. 25 is a diagram for one example of a third indicator indicating a physical age in a watch-type mobile terminal related to the present invention.

FIG. 25 is a diagram for one example of a third indicator indicating a physical age in a watch-type mobile terminal related to the present invention. In particular, FIG. 25 shows that as a preset period expires, a content displayed on a third indicator is changed.

The aforementioned first indicator is an indicator appearing on a watch screen while a user is doing daily activity. And, the aforementioned second indicator corresponds to an indicator appearing on the watch screen if a user completes exercise. Namely, each of the first and second indicators may correspond to an indicator appearing on the display unit based on user's sensed movement instead of appearing every predetermined time period. Yet, the third indicator may correspond to an indicator appearing on the display unit every preset time period irrespective of user's movement.

As described above, the third indicator may be displayed in various forms. For example, the third indicator may be displayed as a human face image or a physical age text. Referring to FIG. 25(a), if a user wearing a mobile terminal goes to work by taking exercise such as running, a physical age may be determined as younger than an actual age by 1 year. In this case, as shown in the top of FIG. 25(a), the mobile terminal can display '−1 yr' on the third indicator. Moreover, in this case, as shown in the bottom of FIG. 25(a), the mobile terminal can display a face image looking younger than a user's actual age on the third indicator.

Referring to FIG. 25(b), after expiration of about 2 hours since the mobile terminal wearing user goes to work, since exercise cannot be taken due to business hours, a physical age may be determined as older than the user's actual age by 3 years. In this case, as shown in the top of FIG. 25(b), the mobile terminal can display '+3 yr' on the third indicator. Moreover, in this case, as shown in the bottom of FIG. 25(b), the mobile terminal can display a face image looking older than the user's actual age on the third indicator.

Referring to FIG. 25(c), if the mobile terminal wearing user takes exercise on a lunch time, a physical age may be determined as younger than the user's actual age by 1 year. In this case, as shown in the top of FIG. 25(c), the mobile terminal can display '−1 yr' on the third indicator. Moreover, in this case, as shown in the bottom of FIG. 25(c), the mobile terminal can display a face image looking younger than the user's actual age on the third indicator.

Referring to FIG. 25(d), since the mobile terminal wearing user is unable to take exercise due to afternoon business hours, a physical age may be determined as older than the user's actual age by 3 years. In this case, as described in FIG. 25(b), the mobile terminal can display, as shown in the bottom of FIG. 25(d), '+3 yr' or a face image looking older than the user's actual age on the third indicator.

Referring to FIG. 25(e), if the mobile terminal wearing user does not take exercise or daily activity after getting off work, a physical age may be determined as older than the user's actual age by 5 years. In this case, as shown in the top of FIG. 25(e), the mobile terminal can display '+5 yr' on the third indicator. Moreover, in this case, as shown in the bottom of FIG. 25(e), the mobile terminal can display a face image looking much older than the user's actual age on the third indicator.

Meanwhile, the case of the aforementioned embodiment corresponds to a case that the preset period amounts to about 2 hours, by which the embodiment is non-limited. Namely, if the preset period is a month, the mobile terminal may display the third indicator on the watch screen every month. Moreover, if the preset period is a year, the mobile terminal may display the third indicator on the watch screen every year. Therefore, a user can be aware of a physical age of the user through the third indicator displayed by the preset periods, thereby being motivated to take exercise.

Figure 26:
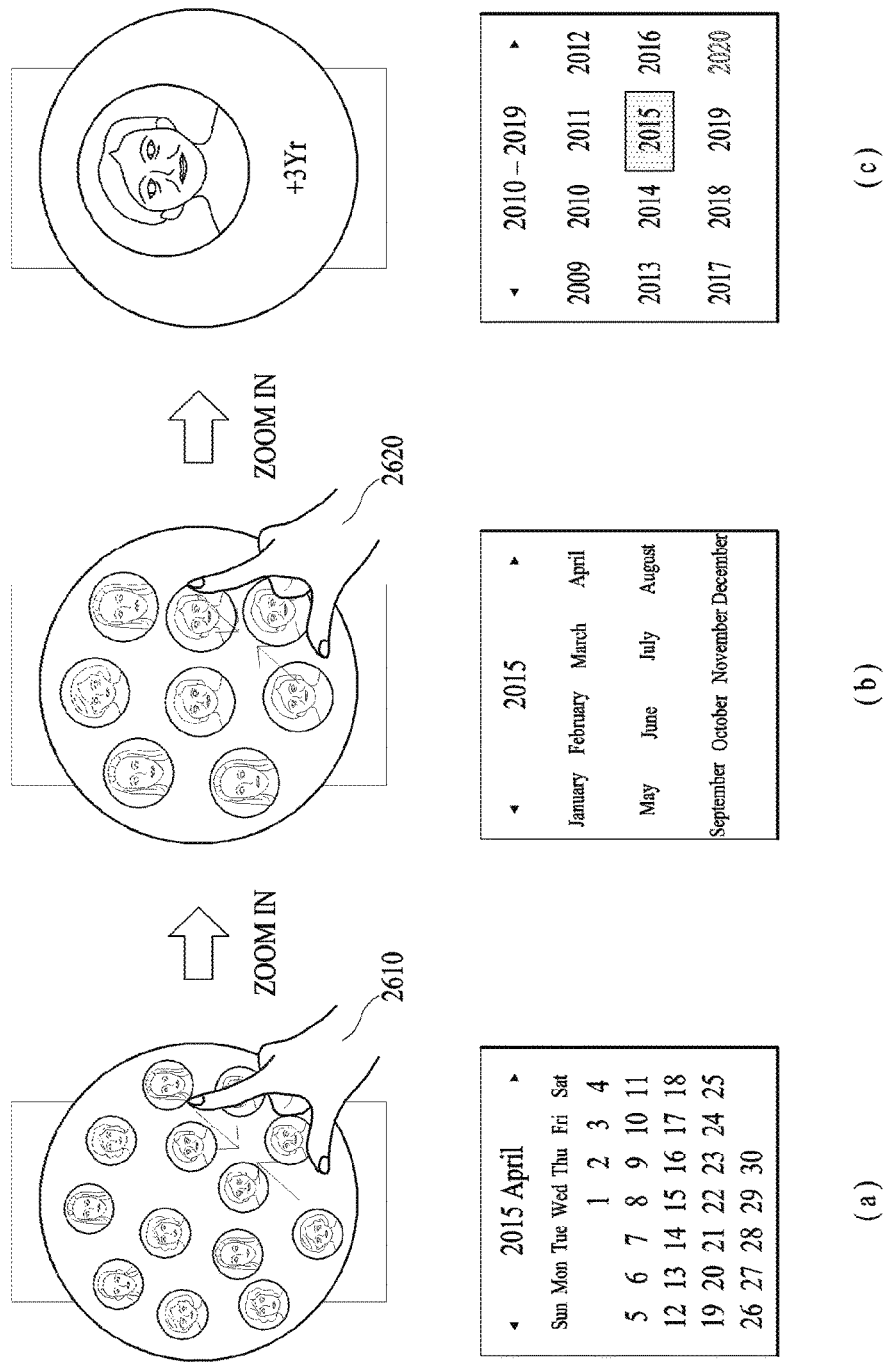
FIG. 26 is a diagram for one example of a third indicator indicating a physical age in a watch-type mobile terminal related to the present invention.

FIG. 26 is a diagram for one example of a third indicator indicating a physical age in a watch-type mobile terminal related to the present invention. In particular, FIG. 26 shows that if a third indicator is displayed by preset periods, it is displayed by being linked to a calendar application.

Referring to FIG. 26(a), a plurality of third indicators, each of which indicates a physical age by day units, can be simultaneously displayed. Namely, to correspond to the calendar of April 2015 shown in the bottom of FIG. 26(a), 30 third indicators included in April can be simultaneously displayed. Through this, a user can see the distribution of physical ages of April 2015 at a time.

In this case, the user may desire to recognize a user's physical age not by day units but by month units. If so, as shown in FIG. 26(a), a mobile terminal may sense a first input signal 2610. Here, the first input signal 2610 may correspond to a pinch-in touch input to a display unit. For example, the pinch-in touch input may correspond to a touch input applied in a manner that a distance between 2 pointers sensed by the display unit is decreased. Moreover, the first input signal 2610 may correspond to an input signal for reducing a content displayed on the display unit.

In this case, as shown in the top of FIG. 26(b), a plurality of third indicators, each of which indicates a physical age by month units, can be simultaneously displayed. Namely, to correspond to the month-unit calendar of 2015, 12 third indicators included in 2015 can be simultaneously displayed. Here, the third indicator of the month unit may correspond to an average of day-unit indicators corresponding to each month. Here, the third indicator of the month unit may have a size greater than that of the third indicator of the day unit. Through this, the user can see the distribution of physical ages of the month unit of 2015.

Moreover, a user may desire to recognize a user's physical age not by month units but by year units. If so, as shown in FIG. 26(b), a mobile terminal may sense a second input signal 2620. Here, the second input signal 2620 may correspond to a pinch-in touch input to the display unit. Moreover, the second input signal 2620 may correspond to an input signal for reducing a content displayed on the display unit.

In this case, as shown in the top of FIG. 26(c), a third indicator indicating a physical age by year unit can be displayed. Namely, to correspond to 2015 shown in the bottom of FIG. 26(c), a third indicator representing 2015 can be displayed. Here, the third indicator of the year unit may correspond to an average of month-unit indicators. In this case, the third indicator of the year unit may have a size greater than that of the third indicator of the month unit. Through this, the user can see an average physical age for 1 year.

Meanwhile, based on a length of the pinch-in touch input, the mobile terminal may display a third indicator of 1-year unit directly from a third indicator of day unit [not shown in FIG. 26].

Moreover, if sensing a pinch-out touch input to the third indicator indicating the physical age by 1-year unit shown in FIG. 26(c), the mobile terminal may display a plurality of the third indicators of the month unit shown in FIG. 26(b) on the display unit [not shown in FIG. 26]. For example, the pinch-out touch input may correspond to a touch input applied in a manner that a distance between 2 pointers sensed by the display unit is increased.

Figure 27:
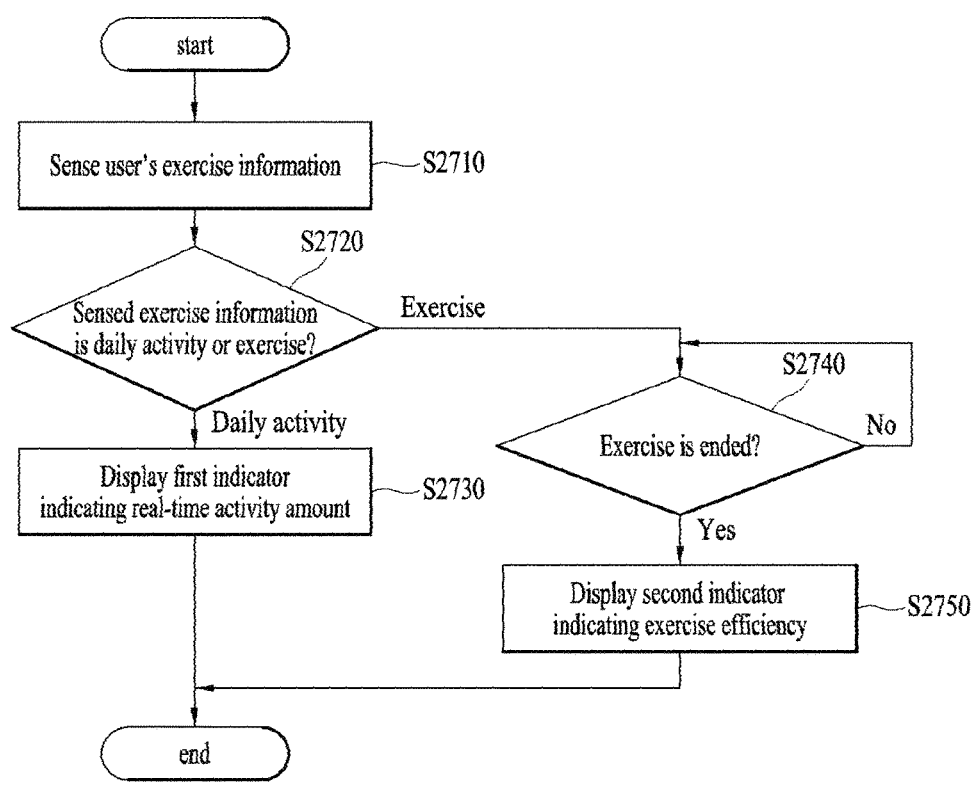
FIG. 27 is a flowchart for a method of controlling a watch-type mobile terminal related to the present invention.

FIG. 27 is a flowchart for a method of controlling a watch-type mobile terminal related to the present invention. Each step of the following description in FIG. 27 can be controlled by the controller of the mobile terminal shown in FIG. 1.

First of all, a mobile terminal can sense user's exercise information [S2710]. Regarding this, as described in FIG. 11, the exercise information may correspond to at least one of a movement of the mobile terminal, a heart rate of the user wearing the mobile terminal, a moving speed of the mobile terminal, a travel distance of the mobile terminal, an altitude of the mobile terminal, an inclination of the mobile terminal, and an acceleration of the mobile terminal.

Subsequently, the mobile terminal can determine whether the sensed exercise information is daily activity or exercise [S2720]. As described above, whether the sensed exercise information is daily activity or exercise can be determined according to a case that at least one of the sensed exercise informations corresponds to a preset range. For example, if the user's exercise information corresponds to the preset range, it may correspond to the exercise. For example, if the user's exercise information fails to correspond to the preset range, it may correspond to the daily activity.

If the sensed exercise information is the daily activity in the step S2720, the mobile terminal can display a first indicator indicating a real-time activity amount [S2730]. As described in FIG. 6, the first indicator may include a first activity amount and a second activity amount. The first activity amount may indicate activity performed for a unit time by a user. And, the second activity amount may indicate an activity amount resulting from subtracting the first activity amount from a goal activity amount when the goal activity amount is set to 100. Moreover, as described in FIG. 8, the first indicator may further include a third activity amount. Here, the third activity amount may correspond to a part that is not admitted as activity despite a user has moved.

Meanwhile, if the sensed exercise information is the exercise in the step S2720, the mobile terminal may determine whether the exercise is ended [S2740]. As described in FIG. 20, if it corresponds to 'after end of exercise', it may correspond to a case that there is no movement of a user for a preset time. Moreover, a case that it corresponds to 'after end of exercise' may correspond to a case that user's movement rapidly decreases.

If the exercise is ended in the step S2740, the mobile terminal may display a second indicator indicating exercise efficiency [S2750]. As described in FIG. 22, the second indicator may include an average line and a line indicating user's exercise efficiency. The average line indicates an average of exercise efficiency and can be set by various references. For example, the average line may correspond to user's average exercise efficiency based on user's past physical strength and exercise. Moreover, for example, the average line may correspond to average exercise efficiency based on standard physical strength of person of the same age group. Moreover, for example, the average line may be determined on the basis of user's exercise goal.

FIG. 28 is a flowchart for a method of controlling a watch-type mobile terminal related to the present invention. Each step of the following description in FIG. 28 can be controlled by the controller of the mobile terminal shown in FIG. 1. Moreover, in each embodiment of FIG. 28, details of parts, which are identical to or correspond to the aforementioned embodiment of FIG. 27, shall be omitted.

First of all, a mobile terminal can determine whether exercise information is sensed [S2810]. If the exercise information is sensed in the step S2810, the mobile terminal can determine whether the sensed exercise information is daily activity or exercise [S2820].

If the sensed exercise information is the daily activity in the step S2820, the mobile terminal can display a first indicator indicating a real-time activity amount [S2830]. Meanwhile, if the sensed exercise information is the exercise in the step S2820, the mobile terminal may determine whether the exercise is ended [S2840]. If the exercise is ended in the step S2840, the mobile terminal may display a second indicator indicating exercise efficiency [S2850].

Meanwhile, if the exercise information is not sensed in the step S2810, the mobile terminal can determine whether a preset period expires [S2860]. For example, the preset period can be set variously.

If the preset period expires, the mobile terminal can display a third indicator indicating a physical age [S2870]. Ad described in FIG. 23, the mobile terminal can display the third indicator on the watch screen based on the first indicator and the second indicator. The third indicator may correspond to an indicator appearing on the display unit every preset period irrespective of user's movement. The third indicator may correspond to an indicator appearing on the display unit every preset period irrespective of user's movement. The third indicator can be displayed in various forms, and may be displayed as a human face image or a physical age text for example.

Meanwhile, according to the embodiment of the present invention, if the exercise information is not sensed, the third indicator is displayed. Yet, even if the exercise information is sensed, as the preset period expires, the third indicator may be displayed on the watch screen simultaneously with or separately from the first or second indicator.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal. The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

INDUSTRIAL APPLICABILITY

The present invention can be reiteratively performed by a watch-type mobile terminal and method for controlling the same.

What is claimed is:

1. A watch-type mobile terminal, comprising:
a display;
a sensor configured to detect a user's activity information; and
a controller configured to:
determine whether the detected activity information corresponds to a first state of regular activity of the user or to a second state of user exercise;
when the detected activity information corresponds to the first state, cause the display to display a first indicator indicating a real-time activity amount; and
when the detected activity information corresponds to the second state, cause the display to display a second indicator indicating exercise efficiency of the user;
wherein the controller is further configured to cause the display to display, via a displayed photo of the user, a third indicator indicating a physically equivalent age of the user based on the detected activity information, the exercise efficiency, and daily life vitality of the user, during an evaluation of the user's overall life cycle.

2. The watch-type mobile terminal of claim 1, wherein the controller is further configured to determine when the user exercise has ended and continue to cause the display to display the second indicator after the user exercise has ended.

3. The watch-type mobile terminal of claim 1, wherein the detected activity information comprises at least a movement of the watch-type mobile terminal, a heart rate of the user, a moving speed of the watch-type mobile terminal, a moving distance of the watch-type mobile terminal, an altitude of the watch-type mobile terminal, an inclination of the watch-type mobile terminal, or an acceleration of the watch-type mobile terminal.

4. The watch-type mobile terminal of claim 3, wherein the first state or second state is determined based on the detected activity information corresponding to a preset range.

5. The watch-type mobile terminal of claim 1, wherein:
the first indicator indicates at least a real-time activity of the user, an activity goal of the user, an activity deficiency of the user; and
the activity deficiency of the user corresponds to detected movement of the watch-type mobile terminal that is designated as non-active movement of the user.

6. The watch-type mobile terminal of claim 5, wherein when the activity deficiency is reduced by additional detected activity of the user, the controller is further configured to cause the display to display a compensation indicator.

7. The watch-type mobile terminal of claim 1, further comprising a communication unit configured to transmit and receive signals to and from an external device, wherein the controller is further configured to:
receive a first input to the first indicator; and
cause the communication unit to transmit information corresponding to a received first input to the external device to cause detailed information of the real-time activity amount of the user to be displayed at the external device.

8. The watch-type mobile terminal of claim 7, wherein the controller is further configured to:
receive a second input to the first indicator; and
cause the communication unit to transmit information corresponding to the second input to the external device to cause an exercise guide to be displayed at the external device, wherein the exercise guide is based on an activity deficiency of the user.

9. The watch-type mobile terminal of claim 1, wherein the controller is further configured to cause the display to display an exercise guide for reaching an activity goal in response to a touch input to the first indicator.

10. The watch-type mobile terminal of claim 9, wherein the exercise guide is displayed differently based on at least a current time, a current location, or current weather.

11. The watch-type mobile terminal of claim 1, wherein the controller is further configured to cause the display to display an alarm indicator indicating exercise to be performed at a preset time.

12. The watch-type mobile terminal of claim 1, wherein the controller is further configured to change the displayed second indicator when additional activity information of the user is detected.

13. The watch-type mobile terminal of claim 1, wherein the second indicator comprises an indicator indicating a reference exercise efficiency.

14. The watch-type mobile terminal of claim 1, wherein the exercise efficiency is determined based on a standard exercise efficiency corresponding to an age group of the user.

15. A method of controlling a watch-type mobile terminal, comprising:
detecting a user's activity information;
determining whether the detected activity information corresponds to a first state of regular activity of the user or to a second state of user exercise;
displaying a first indicator indicating a real-time activity amount when the detected activity information corresponds to the first state;
displaying a second indicator indicating exercise efficiency of the user when the detected activity information corresponds to the second state; and
displaying, via a displayed photo of the user, a third indicator indicating a physically equivalent age of the user based on the detected activity information, the exercise efficiency, and daily life vitality of the user, during an evaluation of the user's overall life cycle.

16. The method of claim 15, further comprising:
determining the user exercise has ended; and
continuing to display the second indicator after the user exercise has ended.

* * * * *